United States Patent
Tan et al.

(10) Patent No.: US 12,006,550 B2
(45) Date of Patent: *Jun. 11, 2024

(54) TARGETING TREATMENT FOR ADAM30 IN PATHOLOGICAL CELLS

(71) Applicant: University of South Carolina, Columbia, SC (US)

(72) Inventors: Wenbin Tan, Columbia, SC (US); Elaine G. Taine, Columbia, SC (US); Hui Wang, Wuhan (CN); Vi Nguyen, Columbia, SC (US); Xiaoling Cao, Columbia, SC (US)

(73) Assignee: University of South Carolina, Columbia, SC (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/400,308

(22) Filed: Aug. 12, 2021

(65) Prior Publication Data

US 2022/0112559 A1 Apr. 14, 2022

Related U.S. Application Data

(60) Provisional application No. 63/090,382, filed on Oct. 12, 2020.

(51) Int. Cl.
*C12Q 1/6883* (2018.01)
*C07K 16/28* (2006.01)

(52) U.S. Cl.
CPC ........ *C12Q 1/6883* (2013.01); *C07K 16/2896* (2013.01); *C07K 2317/76* (2013.01); *C12Q 2600/158* (2013.01)

(58) Field of Classification Search
CPC ............ C12Q 1/6883; C12Q 2600/158; C07K 16/2896; C07K 2317/76
See application file for complete search history.

(56) References Cited

U.S. PATENT DOCUMENTS

| | | |
|---|---|---|
| 4,522,811 A | 6/1985 | Eppstein et al. |
| 4,676,980 A | 6/1987 | Segal et al. |
| 4,683,195 A | 7/1987 | Mullis et al. |
| 4,683,202 A | 7/1987 | Mullis |
| 4,736,866 A | 4/1988 | Leder et al. |
| 4,816,567 A | 3/1989 | Cabilly et al. |
| 4,870,009 A | 9/1989 | Evans et al. |
| 4,873,191 A | 10/1989 | Wagner et al. |
| 4,873,316 A | 10/1989 | Meade et al. |
| 4,946,778 A | 8/1990 | Ladner et al. |
| 5,223,409 A | 6/1993 | Ladner et al. |
| 5,225,539 A | 7/1993 | Winter |
| 5,272,057 A | 12/1993 | Smulson et al. |
| 5,283,317 A | 2/1994 | Saifer et al. |
| 5,328,470 A | 7/1994 | Nabel et al. |
| 5,459,039 A | 10/1995 | Modrich et al. |
| 5,493,531 A | 2/1996 | Pascucci et al. |
| 5,545,806 A | 8/1996 | Lonberg et al. |
| 5,545,807 A | 8/1996 | Surani et al. |
| 5,569,825 A | 10/1996 | Lonberg et al. |
| 5,625,126 A | 4/1997 | Lonberg et al. |
| 5,633,425 A | 5/1997 | Lonberg et al. |
| 5,661,016 A | 8/1997 | Lonberg et al. |
| 5,871,697 A | 2/1999 | Rothberg et al. |
| 5,916,771 A | 6/1999 | Hori et al. |
| 5,939,598 A | 8/1999 | Kucherlapati et al. |
| 2019/0323086 A1* | 10/2019 | Leuthardt ............ C12Q 1/6806 |
| 2019/0371471 A1* | 12/2019 | Tan ........................ G16B 25/10 |

FOREIGN PATENT DOCUMENTS

| | | |
|---|---|---|
| EP | 0308936 | 7/1994 |
| EP | 0264166 | 8/1996 |
| WO | WO1990011354 | 10/1990 |
| WO | WO1991000360 | 1/1991 |
| WO | WO1991001140 | 2/1991 |
| WO | WO1992009688 | 6/1992 |
| WO | WO1992020373 | 11/1992 |
| WO | WO1993004169 | 3/1993 |
| WO | WO1993008829 | 5/1993 |
| WO | WO1994002602 | 2/1994 |
| WO | WO1994010300 | 5/1994 |
| WO | WO1994016101 | 7/1994 |
| WO | WO1994011026 | 8/1994 |
| WO | WO1996027011 | 9/1996 |
| WO | WO1996033735 | 10/1996 |
| WO | WO1996034096 | 10/1996 |
| WO | WO1999053049 | 10/1999 |

OTHER PUBLICATIONS

Applied Biosystems (TaqMan Gene Expression Assays, 2006, pp. 1-24) (Year: 2006).*
MGC Project Team (The Status, Quality, and Expansion of the NIH Full-Length cDNA Project: The Mammalian Gene Collection (MGC), 14: pp. 2121-2127, 2004) (Year: 2004).*
Pyeritz, Reed (Marfan Syndrome and Related Disorders, Emery and Rimoin's Principles of Medical Genetics, 6th, 2013, 153.6.17 Weill-Marchesani Syndrome). (Year: 2013).*

* cited by examiner

*Primary Examiner* — Mark Halvorson
*Assistant Examiner* — Dennis J Sullivan
(74) *Attorney, Agent, or Firm* — Burr & Forman LLP; Douglas L. Lineberry

(57) ABSTRACT

Described herein are methods and systems using ADAM30 as a biomarker to help early diagnosis of congenital malformed vasculatures in children and which can also serve as a companion diagnostic biomarker for malformed vasculatures, as well as a subpopulation of cancer cells, wherein blockage of activity of ADAM30 by a neutralized antibody or inhibitor can be used as a treatment strategy for those ADAM30-positive vascular endothelial cells and cancer cells.

4 Claims, 22 Drawing Sheets
Specification includes a Sequence Listing.

| Vascular anomalies | | | | |
|---|---|---|---|---|
| Vascular tumors | Vascular malformations | | | |
| | Simple | Combined ◊ | of major named vessels | associated with other anomalies |
| Benign<br>Locally aggressive or borderline<br>Malignant | Capillary malformations<br>Lymphatic malformations<br>Venous malformation<br>Arteriovenous malformations*<br>Arteriovenous fistula* | CVM, CLM<br>LVM, CLVM<br>CAVM*<br>CLAVM*<br>others | See details | See list |

FIGURE 1

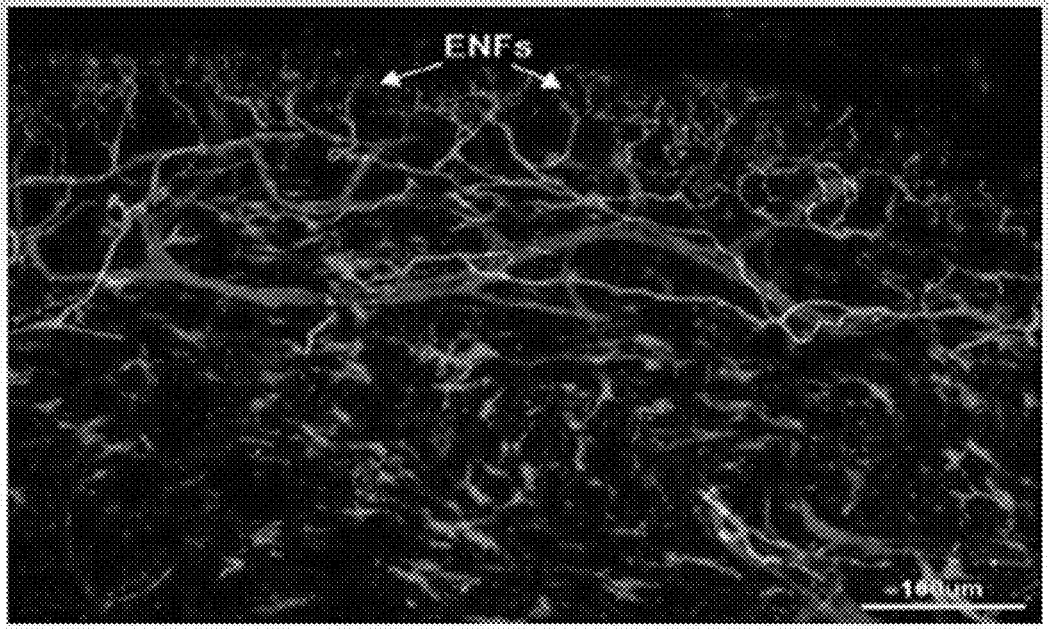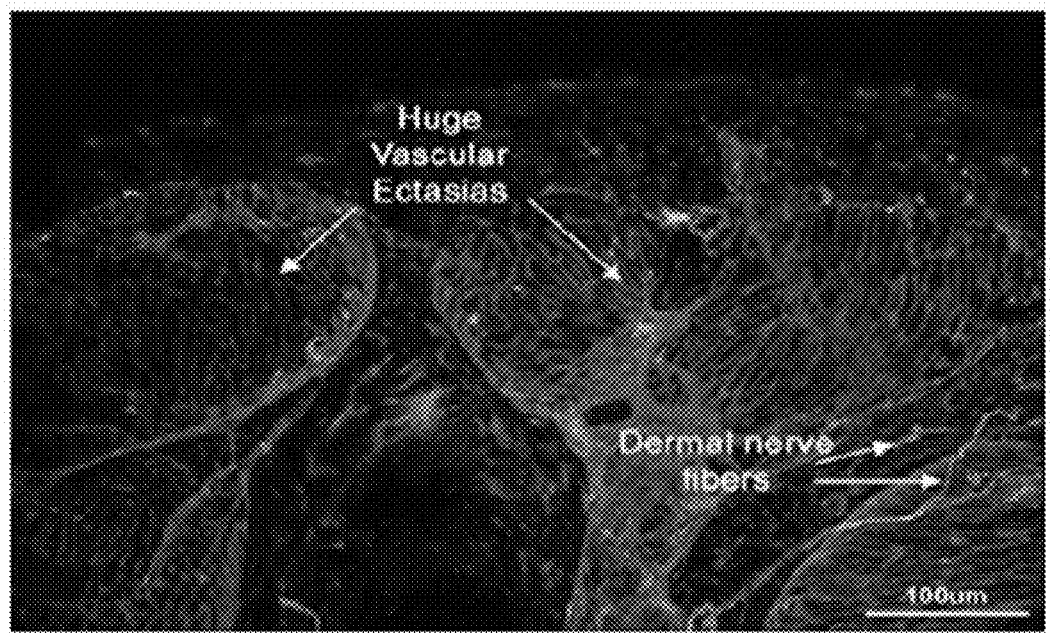
FIGURE 5

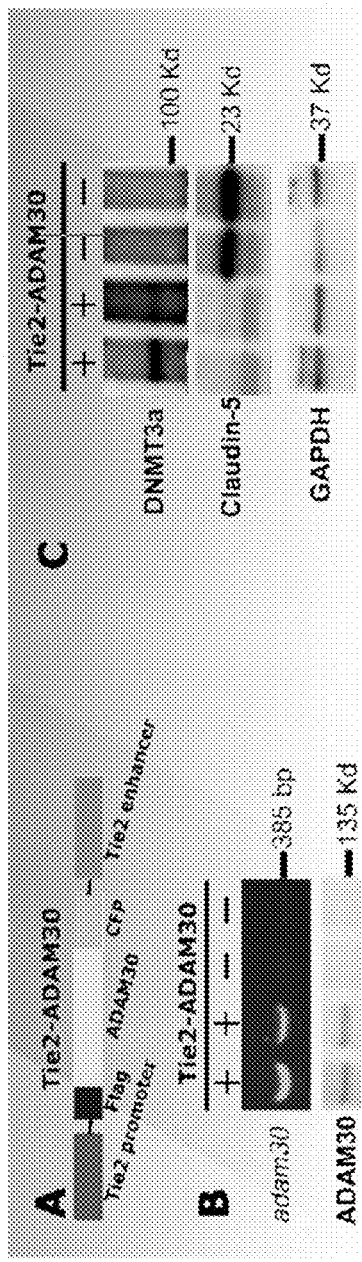 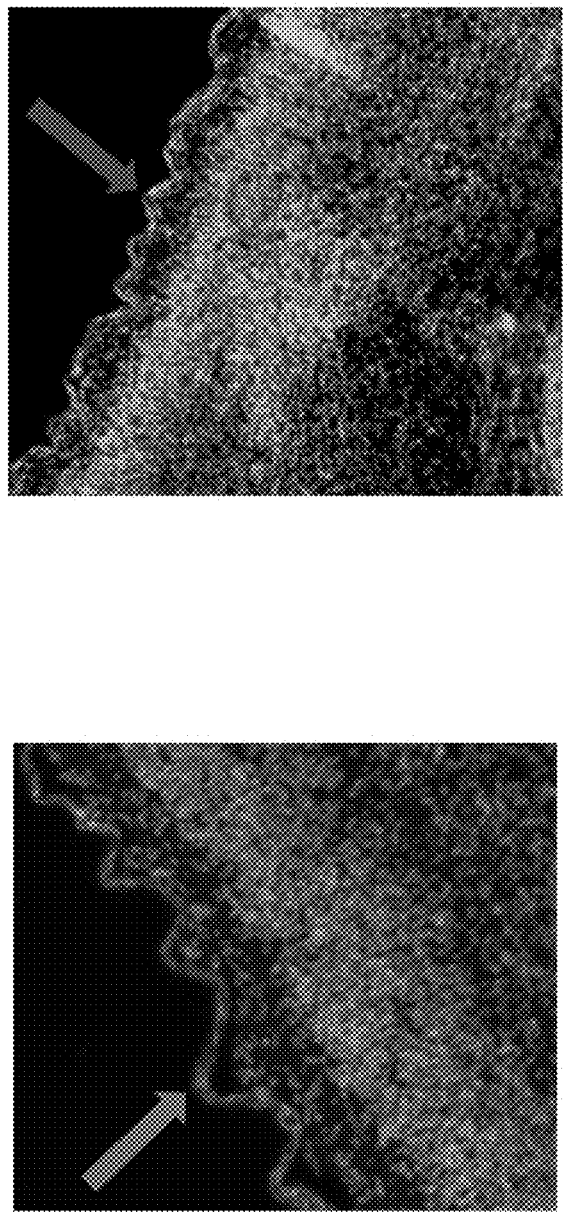
FIGURE 15

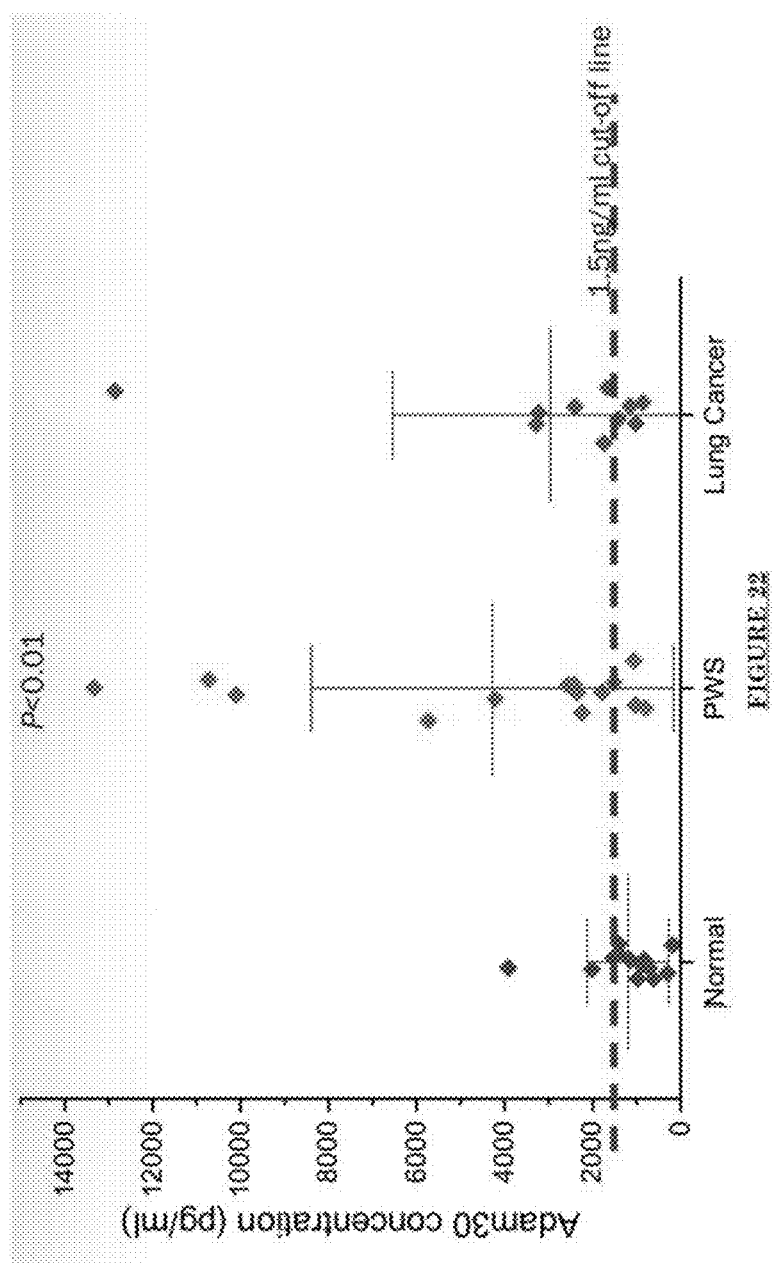

TARGETING TREATMENT FOR ADAM30 IN PATHOLOGICAL CELLS

STATEMENT REGARDING FEDERALLY SPONSORED RESEARCH

This invention was made with government support under RO1 AR073172 awarded by National Institute of Health. The government has certain rights in the invention.

TECHNICAL FIELD

The subject matter disclosed herein is generally directed to methods and systems using ADAM30 as a biomarker to help early diagnosis of congenital malformed vasculatures in children, which can serve as a companion diagnostic biomarker for malformed vasculatures, as well as a subpopulation of cancer cells, wherein blockage of activity of ADAM30 by a neutralized antibody or inhibitor can be used as a treatment strategy for those ADAM30-positive vascular endothelial cells and cancer cells.

BACKGROUND

Congenital vascular malformations occur in 1.5 percent of the general population. Vascular malformations can involve arteries, veins, lymph vessels, capillaries or combinations of these. They occur during embryonic growth, representing vascular defects or developmental problems at birth. Vascular anomalies can be found in any type of blood vessels from any part of the body, such as the extremities, skin, brain, lung, etc. They can be symptomatic or asymptomatic, depending on the locations of the lesions, types of vasculatures involved, and stages of the diseases.

The treatment options for vascular malformations include conservative management, drug treatment, interventional radiology, laser therapy, excisional surgery and psychological treatment. However, due to the complexity of types of blood vessels involved and severity of symptoms, proper diagnosis and management are difficult and prognosis varies, which is a major challenge and threat to public health.

Early diagnosis of some congenital vascular malformations, such as Sturge-Weber Syndrome (SWS) and cerebral vascular malformations are hampered due to lack of biomarkers. The treatment options for these congenital vascular malformations are also very limited and clinical outcomes are not satisfactory. This disclosure can help the early diagnosis for these disorders, as well as provide a novel treatment option for blockage of activity of ADAM30. There is no targeting therapy available so far for these disorders.

Accordingly, it is an object of the present disclosure to provide methods and systems using ADAM30 as a biomarker to help early diagnosis of congenital malformed vasculatures in children, which can also serve as a companion diagnostic biomarker for malformed vasculatures, as well as a subpopulation of cancer cells, wherein blockage of activity of ADAM30 by a neutralized antibody or inhibitor can be used as a treatment strategy for those ADAM30-positive vascular endothelial cells and cancer cells.

Citation or identification of any document in this application is not an admission that such a document is available as prior art to the present disclosure.

SUMMARY

The above objectives are accomplished according to the present disclosure by providing in one embodiment, methods for detecting congenital vascular malformations. The method may include correlating at least one biomarker with at least one congenital vascular malformation, determining the presence of the least one biomarker in a body fluid, and the presence of the at least one biomarker in the body fluid may indicate a presence of at least one congenital vascular malformation. Still, the biomarker may have a genetic sequence of SEQ. ID. NO.: 1. Further, the at least one biomarker may be a disintegrin and metalloproteinase. Again, the method may include identifying Sturge-Weber syndrome via the presence of the at least one biomarker. Further again, the method ma include differentiating cancer cell subtypes via the presence of the at least one biomarker.

In a further embodiment, a method for employing an antibody for treating a congenital vascular malformations is provided. The method may include introducing at least one antibody to at least one vascular endothelial cell and neutralizing enzymatic activity of a protein via binding of the at least one antibody in order to treat at least one congenital vascular malformation. Further, the method may include neutralizing enzymatic activity of a disintegrin and metalloproteinase. Still yet, the method may include neutralizing enzymatic activity of a genetic sequence shown in SEQ. ID. NO.: 1. Further yet, the method may treat Sturge-Weber syndrome. Again further, the may include neutralizing enzymatic activity at location 336-350 of SEQ. ID. NO.: 1. Still yet further, the method may induce antigen immunization in a catalytic domain of SEQ. ID. NO.: 1. Further yet, the method may include introducing the at least one antibody to at least one cancer cell.

These and other aspects, objects, features, and advantages of the example embodiments will become apparent to those having ordinary skill in the art upon consideration of the following detailed description of example embodiments.

BRIEF DESCRIPTION OF THE DRAWINGS

An understanding of the features and advantages of the present disclosure will be obtained by reference to the following detailed description that sets forth illustrative embodiments, in which the principles of the disclosure may be utilized, and the accompanying drawings of which:

FIG. 1 shows a table of vascular malformations.

FIG. 5 shows nerve innervation deficiency in PWS.

FIG. 15 shows Transgenic mouse with an overexpression of ADAM30 in ECs.

FIG. 22 shows ADAM30 levels in patients' serum (by ELISA).

Figure 2:
FIG. 2 shows progressive blood vessel dilatation over time leads to lesion darkening, soft tissue hypertrophy and nodularity.

The figures herein are for illustrative purposes only and are not necessarily drawn to scale.

DETAILED DESCRIPTION OF THE EXAMPLE EMBODIMENTS

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting.

Unless specifically stated, terms and phrases used in this document, and variations thereof, unless otherwise expressly stated, should be construed as open ended as opposed to limiting. Likewise, a group of items linked with the conjunction "and" should not be read as requiring that each and every one of those items be present in the grouping, but rather should be read as "and/or" unless expressly stated otherwise. Similarly, a group of items linked with the conjunction "or" should not be read as requiring mutual exclusivity among that group, but rather should also be read as "and/or" unless expressly stated otherwise.

Furthermore, although items, elements or components of the disclosure may be described or claimed in the singular, the plural is contemplated to be within the scope thereof unless limitation to the singular is explicitly stated. The presence of broadening words and phrases such as "one or more," "at least," "but not limited to" or other like phrases in some instances shall not be read to mean that the narrower case is intended or required in instances where such broadening phrases may be absent.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are cited to disclose and describe the methods and/or materials in connection with which the publications are cited. All such publications and patents are herein incorporated by references as if each individual publication or patent were specifically and individually indicated to be incorporated by reference. Such incorporation by reference is expressly limited to the methods and/or materials described in the cited publications and patents and does not extend to any lexicographical definitions from the cited publications and patents. Any lexicographical definition in the publications and patents cited that is not also expressly repeated in the instant application should not be treated as such and should not be read as defining any terms appearing in the accompanying claims. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Where a range is expressed, a further embodiment includes from the one particular value and/or to the other particular value. The recitation of numerical ranges by endpoints includes all numbers and fractions subsumed within the respective ranges, as well as the recited endpoints. Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

Unless defined otherwise, technical and scientific terms used herein have the same meaning as commonly understood by one of ordinary skill in the art to which this disclosure pertains. Definitions of common terms and techniques in molecular biology may be found in Molecular Cloning: A Laboratory Manual, 2nd edition (1989) (Sambrook, Fritsch, and Maniatis); Molecular Cloning: A Laboratory Manual, 4th edition (2012) (Green and Sambrook); Current Protocols in Molecular Biology (1987) (F. M. Ausubel et al. eds.); the series Methods in Enzymology (Academic Press, Inc.): PCR 2: A Practical Approach (1995) (M. J. MacPherson, B. D. Hames, and G. R. Taylor eds.): Antibodies, A Laboratory Manual (1988) (Harlow and Lane, eds.): Antibodies A Laboratory Manual, 2nd edition 2013 (E. A. Greenfield ed.); Animal Cell Culture (1987) (R. I. Freshney, ed.); Benjamin Lewin, Genes IX, published by Jones and Bartlet, 2008 (ISBN 0763752223); Kendrew et al. (eds.), The Encyclopedia of Molecular Biology, published by Blackwell Science Ltd., 1994 (ISBN 0632021829); Robert A. Meyers (ed.), Molecular Biology and Biotechnology: a Comprehensive Desk Reference, published by VCH Publishers, Inc., 1995 (ISBN 9780471185710); Singleton et al., Dictionary of Microbiology and Molecular Biology 2nd ed., J. Wiley & Sons (New York, N.Y. 1994), March, Advanced Organic Chemistry Reactions, Mechanisms and Structure 4th ed., John Wiley & Sons (New York, N.Y. 1992); and Marten H. Hofker and Jan van Deursen, Transgenic Mouse Methods and Protocols, 2nd edition (2011).

As used herein, the singular forms "a", "an", and "the" include both singular and plural referents unless the context clearly dictates otherwise.

As used herein, "about," "approximately," "substantially," and the like, when used in connection with a measurable variable such as a parameter, an amount, a temporal duration, and the like, are meant to encompass variations of and from the specified value including those within experimental error (which can be determined by e.g. given data set, art accepted standard, and/or with e.g. a given confidence interval (e.g. 90%, 95%, or more confidence interval from the mean), such as variations of +/−10% or less, +/−5% or less, +/−1% or less, and +/−0.1% or less of and from the specified value, insofar such variations are appropriate to perform in the disclosure. As used herein, the terms "about," "approximate," "at or about," and "substantially" can mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, a "biological sample" may contain whole cells and/or live cells and/or cell debris. The biological sample may contain (or be derived from) a "bodily fluid". The present disclosure encompasses embodiments wherein the bodily fluid is selected from amniotic fluid, aqueous humour, vitreous humour, bile, blood serum, breast milk, cerebrospinal fluid, cerumen (earwax), chyle, chyme, endolymph, perilymph, exudates, feces, female ejaculate, gastric acid, gastric juice, lymph, mucus (including nasal drainage and phlegm), pericardial fluid, peritoneal fluid, pleural fluid, pus, rheum, saliva, sebum (skin oil), semen, sputum, synovial fluid, sweat, tears, urine, vaginal secretion, vomit and mixtures of one or more thereof. Biological samples include cell cultures, bodily fluids, cell cultures from bodily fluids. Bodily fluids may be obtained from a mammal organism, for example by puncture, or other collecting or sampling procedures.

As used herein, "agent" refers to any substance, compound, molecule, and the like, which can be administered to a subject on a subject to which it is administered to. An agent can be inert. An agent can be an active agent. An agent can be a primary active agent, or in other words, the component(s) of a composition to which the whole or part of the effect of the composition is attributed. An agent can be a secondary agent, or in other words, the component(s) of a composition to which an additional part and/or other effect of the composition is attributed.

As used herein, "active agent" or "active ingredient" refers to a substance, compound, or molecule, which is biologically active or otherwise, induces a biological or physiological effect on a subject to which it is administered to. In other words, "active agent" or "active ingredient" refers to a component or components of a composition to which the whole or part of the effect of the composition is attributed.

As used herein, "administering" refers to any suitable administration for the agent(s) being delivered and/or subject receiving said agent(s) and can be oral, topical, intravenous, subcutaneous, transcutaneous, transdermal, intramuscular, intra-joint, parenteral, intra-arteriole, intradermal, intraventricular, intraosseous, intraocular, intracranial, intraperitoneal, intralesional, intranasal, intracardiac, intraarticular, intracavernous, intrathecal, intravireal, intracerebral, and intracerebroventricular, intratympanic, intracochlear, rectal, vaginal, by inhalation, by catheters, stents or via an implanted reservoir or other device that administers, either actively or passively (e.g. by diffusion) a composition the perivascular space and adventitia. For example, a medical device such as a stent can contain a composition or formulation disposed on its surface, which can then dissolve or be otherwise distributed to the surrounding tissue and cells. The term "parenteral" can include subcutaneous, intravenous, intramuscular, intra-articular, intra-synovial, intrasternal, intrathecal, intrahepatic, intralesional, and intracranial injections or infusion techniques. Administration routes can be, for instance, auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intra abdominal, intra-amniotic, intra-arterial, intra-articular, intrabiliary, intrabronchial, intrabursal, intracardiac, intracartilaginous, intracaudal, intracavernous, intracavity, intracerebral, intracisternal, intracorneal, intracoronal (dental), intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratym panic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, other, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmucosal, transplacental, transtracheal, transtympanic, ureteral, urethral, and/or vaginal administration, and/or any combination of the above administration routes, which typically depends on the disease to be treated, subject being treated, and/or agent(s) being administered.

As used herein "cancer" can refer to one or more types of cancer including, but not limited to, acute lymphoblastic leukemia, acute myeloid leukemia, adrenocortical carcinoma, Kaposi Sarcoma, AIDS-related lymphoma, primary central nervous system (CNS) lymphoma, anal cancer, appendix cancer, astrocytomas, atypical teratoid/Rhabdoid tumors, basa cell carcinoma of the skin, bile duct cancer, bladder cancer, bone cancer (including but not limited to Ewing Sarcoma, osteosarcomas, and malignant fibrous histiocytoma), brain tumors, breast cancer, bronchial tumors, Burkitt lymphoma, carcinoid tumor, cardiac tumors, germ cell tumors, embryonal tumors, cervical cancer, cholangiocarcinoma, chordoma, chronic lymphocytic leukemia, chronic myelogenous leukemia, chronic myeloproliferative neoplasms, colorectal cancer, craniopharyngioma, cutaneous T-Cell lymphoma, ductal carcinoma in situ, endometrial cancer, ependymoma, esophageal cancer, esthesioneuroblastoma, extracranial germ cell tumor, extragonadal germ cell tumor, eye cancer (including, but not limited to, intraocular melanoma and retinoblastoma), fallopian tube cancer, gallbladder cancer, gastric cancer, gastrointestinal carcinoid tumor, gastrointestinal stromal tumors, central nervous system germ cell tumors, extracranial germ cell tumors, extragonadal germ cell tumors, ovarian germ cell tumors, testicular cancer, gestational trophoblastic disease, Hairy cell leukemia, head and neck cancers, hepatocellular (liver) cancer, Langerhans cell histiocytosis, Hodgkin lymphoma, hypopharyngeal cancer, islet cell tumors, pancreatic neuroendocrine tumors, kidney (renal cell) cancer, laryngeal cancer, leukemia, lip cancer, oral cancer, lung cancer (non-small cell and small cell), lymphoma, melanoma, Merkel cell carcinoma, mesothelioma, metastatic squamous cell neck cancer, midline tract carcinoma with and without NUT gene changes, multiple endocrine neoplasia syndromes, multiple myeloma, plasma cell neoplasms, mycosis fungoides, myelodyspastic syndromes, myelodysplastic/myeloproliferative neoplasms, chronic myelogenous leukemia, nasal cancer, sinus cancer, non-Hodgkin lymphoma, pancreatic cancer, paraganglioma, paranasal sinus cancer, parathyroid cancer, penile cancer, pharyngeal cancer, pheochromocytoma, pituitary cancer, peritoneal cancer, prostate cancer, rectal cancer, Rhabdomyosarcoma, salivary gland cancer, uterine sarcoma, Sezary syndrome, skin cancer, small intestine cancer, large intestine cancer (colon cancer), soft tissue sarcoma, T-cell lymphoma, throat cancer, oropharyngeal cancer, nasopharyngeal cancer, hypopharyngeal cancer, thymoma, thymic carcinoma, thyroid cancer, transitional cell cancer of the renal pelvis and ureter, urethral cancer, uterine cancer, vaginal cancer, cervical cancer, vascular tumors and cancer, vulvar cancer, and Wilms Tumor.

As used herein, "chemotherapeutic agent" or "chemotherapeutic" refers to a therapeutic agent utilized to prevent or treat cancer.

As used herein, "control" can refer to an alternative subject or sample used in an experiment for comparison purpose and included to minimize or distinguish the effect of variables other than an independent variable.

The term "optional" or "optionally" means that the subsequent described event, circumstance or substituent may or may not occur, and that the description includes instances where the event or circumstance occurs and instances where it does not.

As used herein, "dose," "unit dose," or "dosage" can refer to physically discrete units suitable for use in a subject, each unit containing a predetermined quantity of the Hiroloxamer and/or a pharmaceutical formulation thereof calculated to produce the desired response or responses in association with its administration.

The term "molecular weight", as used herein, can generally refer to the mass or average mass of a material. If a polymer or oligomer, the molecular weight can refer to the relative average chain length or relative chain mass of the bulk polymer. In practice, the molecular weight of polymers and oligomers can be estimated or characterized in various ways including gel permeation chromatography (GPC) or capillary viscometry. GPC molecular weights are reported as the weight-average molecular weight ($M_w$) as opposed to the number-average molecular weight ($M_n$). Capillary viscometry provides estimates of molecular weight as the inherent viscosity determined from a dilute polymer solution using a particular set of concentration, temperature, and solvent conditions.

As used herein, "pharmaceutical formulation" refers to the combination of an active agent, compound, or ingredient with a pharmaceutically acceptable carrier or excipient, making the composition suitable for diagnostic, therapeutic, or preventive use in vitro, in vivo, or ex vivo.

As used herein, "pharmaceutically acceptable carrier or excipient" refers to a carrier or excipient that is useful in preparing a pharmaceutical formulation that is generally safe, non-toxic, and is neither biologically or otherwise undesirable, and includes a carrier or excipient that is acceptable for veterinary use as well as human pharmaceutical use. A "pharmaceutically acceptable carrier or excipient" as used in the specification and claims includes both one and more than one such carrier or excipient.

As used herein, "polymer" refers to molecules made up of monomers repeat units linked together. "Polymers" are understood to include, but are not limited to, homopolymers, copolymers, such as for example, block, graft, random and alternating copolymers, terpolymers, etc. and blends and modifications thereof. "A polymer" can be can be a three-dimensional network (e.g. the repeat units are linked together left and right, front and back, up and down), a two-dimensional network (e.g. the repeat units are linked together left, right, up, and down in a sheet form), or a one-dimensional network (e.g. the repeat units are linked left and right to form a chain). "Polymers" can be composed, natural monomers or synthetic monomers and combinations thereof. The polymers can be biologic (e.g. the monomers are biologically important (e.g. an amino acid), natural, or synthetic.

As used herein, the term "radiation sensitizer" refers to agents that can selectively enhance the cell killing from irradiation in a desired cell population, such as tumor cells, while exhibiting no single agent toxicity on tumor or normal cells.

The terms "subject," "individual," and "patient" are used interchangeably herein to refer to a vertebrate, preferably a mammal, more preferably a human. Mammals include, but are not limited to, murines, simians, humans, farm animals, sport animals, and pets. Tissues, cells and their progeny of a biological entity obtained in vivo or cultured in vitro are also encompassed by the term "subject".

As used herein, "substantially pure" can mean an object species is the predominant species present (i.e., on a molar basis it is more abundant than any other individual species in the composition), and preferably a substantially purified fraction is a composition wherein the object species comprises about 50 percent of all species present. Generally, a substantially pure composition will comprise more than about 80 percent of all species present in the composition, more preferably more than about 85%, 90%, 95%, and 99%. Most preferably, the object species is purified to essential homogeneity (contaminant species cannot be detected in the composition by conventional detection methods) wherein the composition consists essentially of a single species.

As used interchangeably herein, the terms "sufficient" and "effective," can refer to an amount (e.g. mass, volume, dosage, concentration, and/or time period) needed to achieve one or more desired and/or stated result(s). For example, a therapeutically effective amount refers to an amount needed to achieve one or more therapeutic effects.

As used herein, "tangible medium of expression" refers to a medium that is physically tangible or accessible and is not a mere abstract thought or an unrecorded spoken word. "Tangible medium of expression" includes, but is not limited to, words on a cellulosic or plastic material, or data stored in a suitable computer readable memory form. The data can be stored on a unit device, such as a flash memory or CD-ROM or on a server that can be accessed by a user via, e.g. a web interface.

As used herein, "therapeutic" can refer to treating, healing, and/or ameliorating a disease, disorder, condition, or side effect, or to decreasing in the rate of advancement of a disease, disorder, condition, or side effect. A "therapeutically effective amount" can therefore refer to an amount of a compound that can yield a therapeutic effect.

As used herein, the terms "treating" and "treatment" can refer generally to obtaining a desired pharmacological and/or physiological effect. The effect can be, but does not necessarily have to be, prophylactic in terms of preventing or partially preventing a disease, symptom or condition thereof, such as cancer and/or indirect radiation damage. The effect can be therapeutic in terms of a partial or complete cure of a disease, condition, symptom or adverse effect attributed to the disease, disorder, or condition. The term "treatment" as used herein covers any treatment of cancer and/or indirect radiation damage, in a subject, particularly a human and/or companion animal, and can include any one or more of the following: (a) preventing the disease or damage from occurring in a subject which may be predisposed to the disease but has not yet been diagnosed as having it; (b) inhibiting the disease, i.e., arresting its development; and (c) relieving the disease, i.e., mitigating or ameliorating the disease and/or its symptoms or conditions. The term "treatment" as used herein can refer to both therapeutic treatment alone, prophylactic treatment alone, or both therapeutic and prophylactic treatment. Those in need of treatment (subjects in need thereof) can include those already with the disorder and/or those in which the disorder is to be prevented. As used herein, the term "treating", can include inhibiting the disease, disorder or condition, e.g., impeding its progress; and relieving the disease, disorder, or condition, e.g., causing regression of the disease, disorder and/or condition. Treating the disease, disorder, or condition can include ameliorating at least one symptom of the particular disease, disorder, or condition, even if the underlying pathophysiology is not affected, such as treating the pain of a subject by administration of an analgesic agent even though such agent does not treat the cause of the pain.

As used herein, the terms "weight percent," "wt %," and "wt. %," which can be used interchangeably, indicate the percent by weight of a given component based on the total weight of a composition of which it is a component, unless otherwise specified. That is, unless otherwise specified, all wt % values are based on the total weight of the composition. It should be understood that the sum of wt % values for all components in a disclosed composition or formulation are equal to 100. Alternatively, if the wt % value is based on the total weight of a subset of components in a composition, it should be understood that the sum of wt % values the specified components in the disclosed composition or formulation are equal to 100.

As used herein, "water-soluble", as used herein, generally means at least about 10 g of a substance is soluble in 1 L of water, i.e., at neutral pH, at 25° C.

Various embodiments are described hereinafter. It should be noted that the specific embodiments are not intended as an exhaustive description or as a limitation to the broader aspects discussed herein. One aspect described in conjunction with a particular embodiment is not necessarily limited to that embodiment and can be practiced with any other embodiment(s). Reference throughout this specification to "one embodiment", "an embodiment," "an example embodiment," means that a particular feature, structure or characteristic described in connection with the embodiment is included in at least one embodiment of the present disclosure. Thus, appearances of the phrases "in one embodiment," "in an embodiment," or "an example embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the disclosure. For example, in the appended claims, any of the claimed embodiments can be used in any combination.

All patents, patent applications, published applications, and publications, databases, websites and other published materials cited herein are hereby incorporated by reference to the same extent as though each individual publication, published patent document, or patent application was specifically and individually indicated as being incorporated by reference.

Kits

Any of the treatments, compounds and/or formulations described herein can be presented as a combination kit. As used herein, the terms "combination kit" or "kit of parts" refers to the compounds, compositions, formulations, particles, cells and any additional components that are used to package, sell, market, deliver, and/or administer the combination of elements or a single element, such as the active ingredient, contained therein. Such additional components include, but are not limited to, packaging, syringes, blister packages, bottles, and the like. When one or more of the compounds, compositions, formulations, particles, cells, described herein or a combination thereof (e.g., agent(s)) contained in the kit are administered simultaneously, the combination kit can contain the active agent(s) in a single formulation, such as a pharmaceutical formulation, (e.g., a tablet, liquid preparation, dehydrated preparation, etc.) or in separate formulations. When the compounds, compositions, formulations, particles, and cells described herein or a combination thereof and/or kit components are not administered simultaneously, the combination kit can contain each agent or other component in separate pharmaceutical formulations. The separate kit components can be contained in a single package or in separate packages within the kit.

In some embodiments, the combination kit also includes instructions printed on or otherwise contained in a tangible medium of expression. The instructions can provide information regarding the content of the compounds and/or formulations, safety information regarding the content of the compounds and formulations (e.g., pharmaceutical formulations), information regarding the dosages, indications for use, and/or recommended treatment regimen(s) for the compound(s) and/or pharmaceutical formulations contained therein. In some embodiments, the instructions can provide directions and protocols for administering the compounds and/or formulations described herein to a subject in need thereof. In some embodiments, the instructions can provide one or more embodiments of the methods for administration and/or pharmaceutical formulation thereof such as any of the methods described in greater detail elsewhere herein.

This current disclosure describes that ADAM30 can be a biomarker for congenital vascular malformations as well as a subset of cancer patients. This biomarker can be detected in body fluids including blood, CSF, urine etc., to help early diagnosis of congenital vascular malformations or differentiate certain subtypes of cancer cells. ADAM30 can serve as a companion diagnostic biomarker. Inhibition of ADAM30 activity by neutralized antibodies, inhibitors, siRNAs, etc., can be used for the treatment options for ADAM30-positive vascular endothelial cells and cancer cells. This disclosure also describes an anti-ADAM30 antibody, which can neutralize the enzymatic activity of ADAM30. The current disclosure provides the first companion diagnostic biomarker and first targeting treatment option for congenital vascular malformations to help early diagnosis and increase the treatment efficacy. It is also applicable to a subset of cancer cells.

ADAM30, ADAM metallopeptidase domain 30, is a gene that encodes a member of the ADAM (a disintegrin and metalloprotease domain) family. Members of this family are membrane-anchored proteins structurally related to snake venom disintegrins, and have been implicated in a variety of biological processes involving cell-cell and cell-matrix interactions, including fertilization, muscle development, and neurogenesis. This gene is testis-specific and contains a polymorphic region, resulting in isoforms with varying numbers of C-terminal repeats.

Neutralization, or functional blocking, of proteins by antibodies is often used to study biologic function mediated by cell surface expressed proteins. For example, to study the effects of a particular cytokine on cell signaling and other biologic effects, antibodies can be used that will specifically bind and reduce the amount of free cytokine that can bind to receptors; thereby, down regulating its biologic effects. Neutralization testing is one strategy we use to validate antibodies for research use. When used as a tool to test the specificity of antibodies, the rationale is that when an antibody exhibits functional blocking characteristics it is strong evidence that the antibody is binding the intended target and demonstrating that the antibody is specific to its intended target. To determine if neutralization or a functional blocking approach is applicable for specificity testing, one has to rely on a defined system with a measurable output in order to be able to quantify the effects of the blocking function. These systems could be a motility assay, bioactivity assay, or any other measurable activity.

Figure 3:
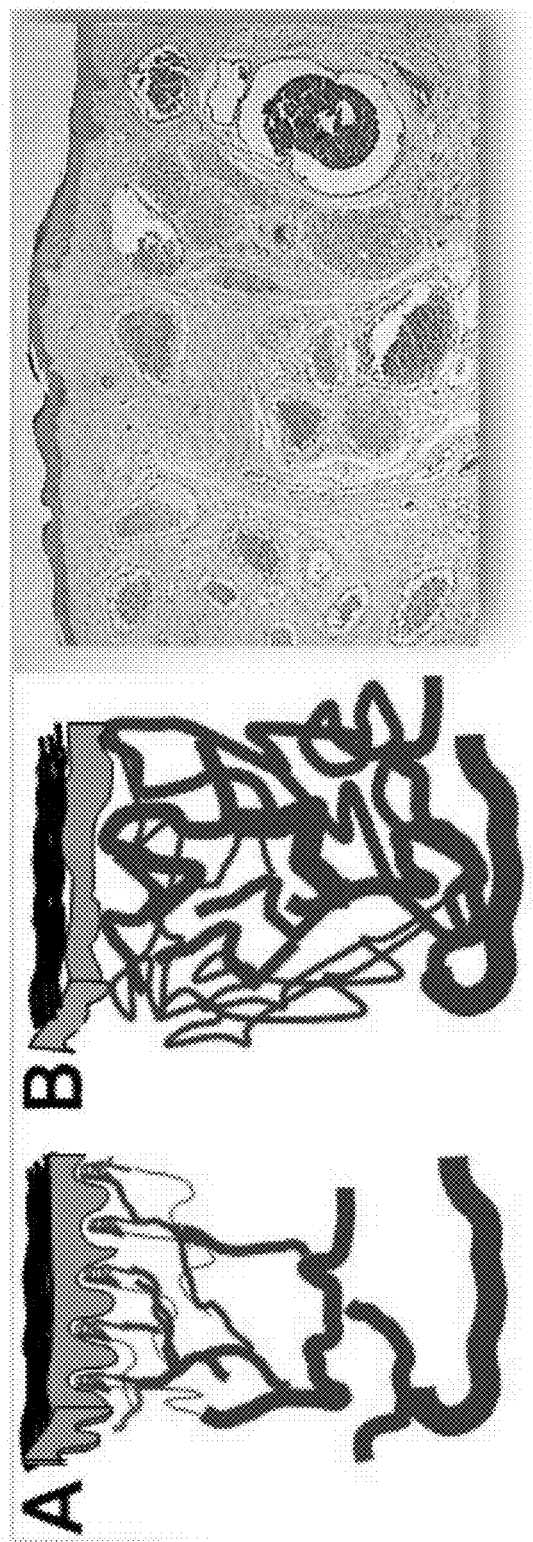
FIG. 3 shows PWS vascular pathology: progressive dilatation.
Figure 4:
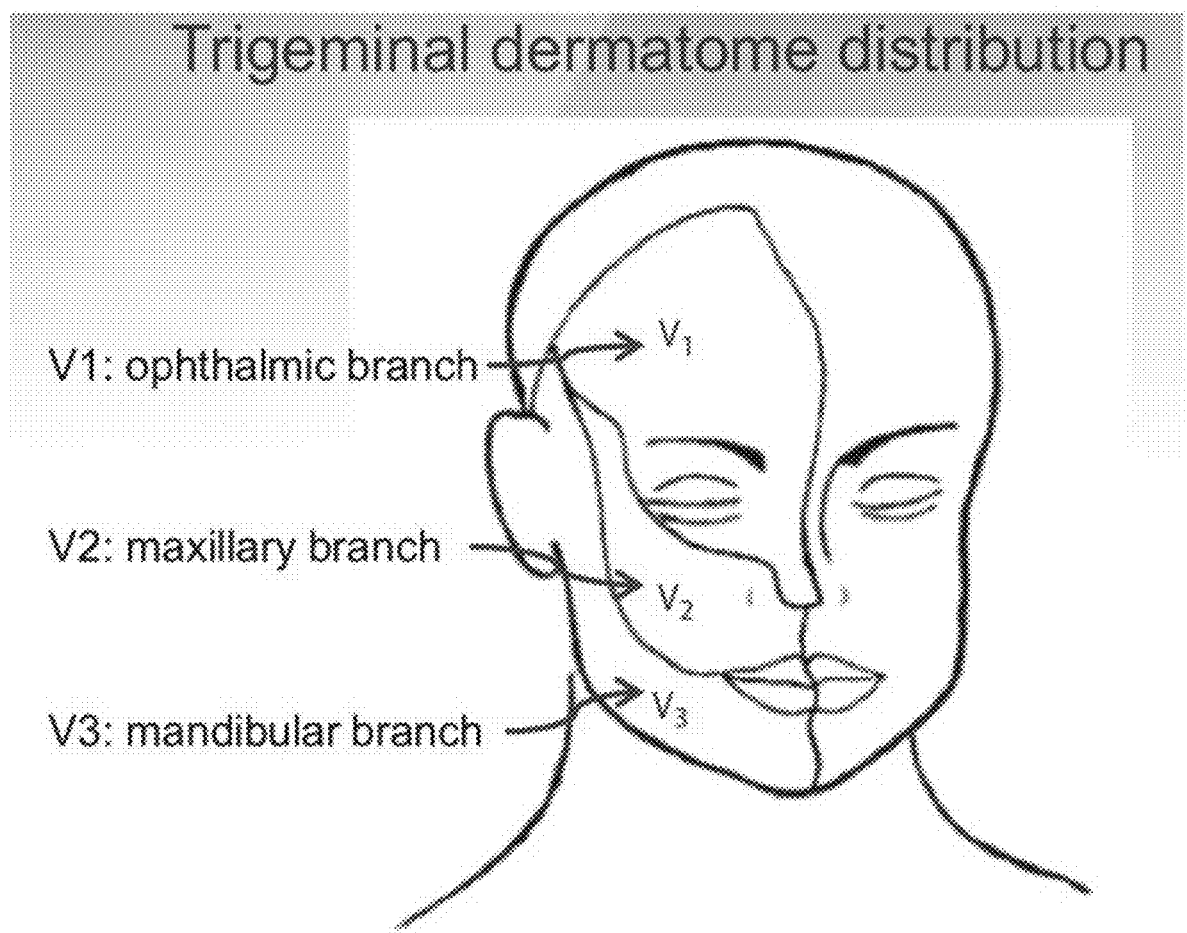
FIG. 4 shows trigeminal dermatome distribution.

FIG. 1 shows a table of vascular malformations. FIG. 2 shows skin lesions of Port Wine Stain (PWS): Progressive Skin Vascular Malformations. Progressive blood vessel dilatation over time leads to lesion darkening, soft tissue hypertrophy and nodularity. FIG. 3 shows PWS vascular pathology: progressive dilatation. FIG. 4 shows trigeminal dermatome distribution. FIG. 5 shows nerve innervation deficiency in PWS.

One significant impact of the current disclosure will be the ability to detect Sturge-Weber Syndrome (SWS). SWS is a congenital, neurological disorder indicated at birth by a PWS birthmark on the forehead and upper eyelid of one side of the face (V1 branch); the incidence and cause are unknown. Generally, about 20%-50% upper facial PWS are associated with SWS. Further, cerebral vascular malformations typically develop on the back (occipital) region of the brain on the same side as the port wine birthmark. Seizures occur in 72% to 80% of SWS patients; Glaucoma occurs in 30% to 71% of the patients. The current disclosure provides heretofore unknown diagnostic and treatment regimes for such conditions.

Figure 6:
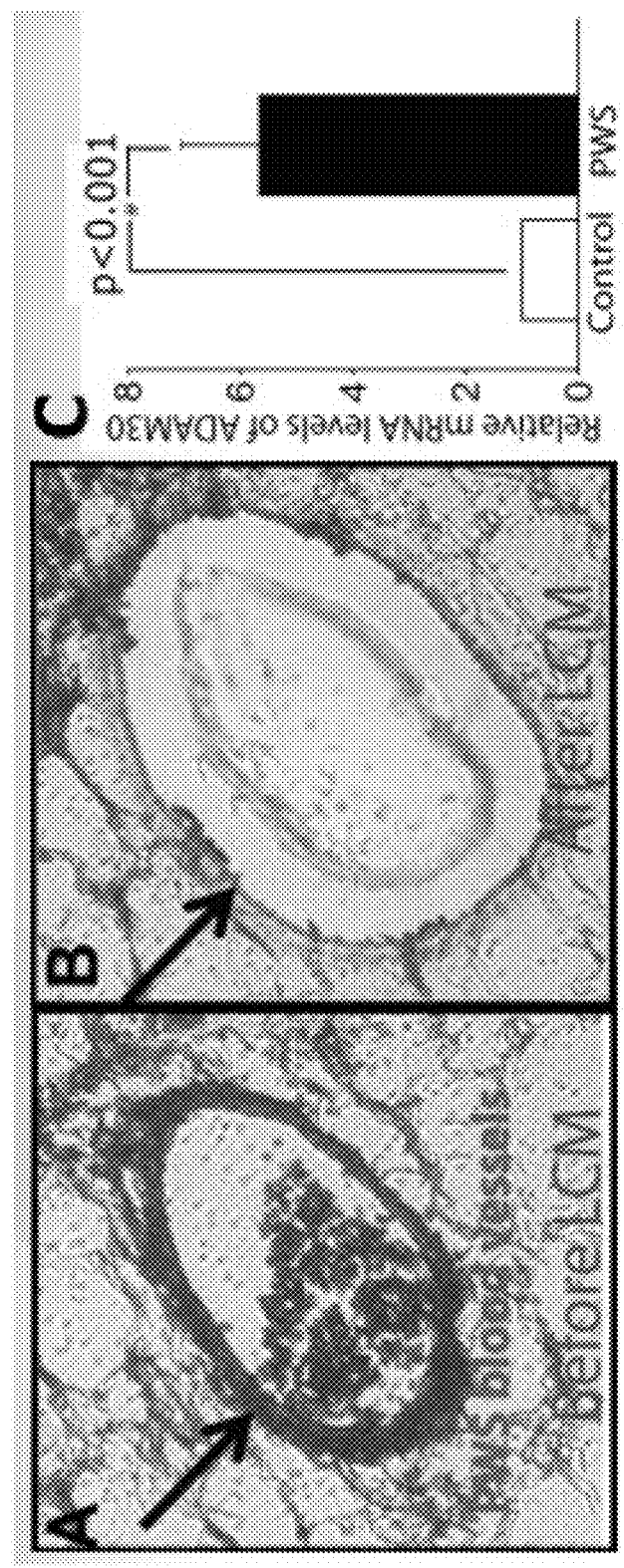
FIG. 6 shows ADAM30 mRNA increases in PWS blood vessels.

FIG. 6 shows ADAM30 mRNA increases in PWS blood vessels via laser capture microdissection (LCM)/RNA-Seq analysis.

Figure 7:
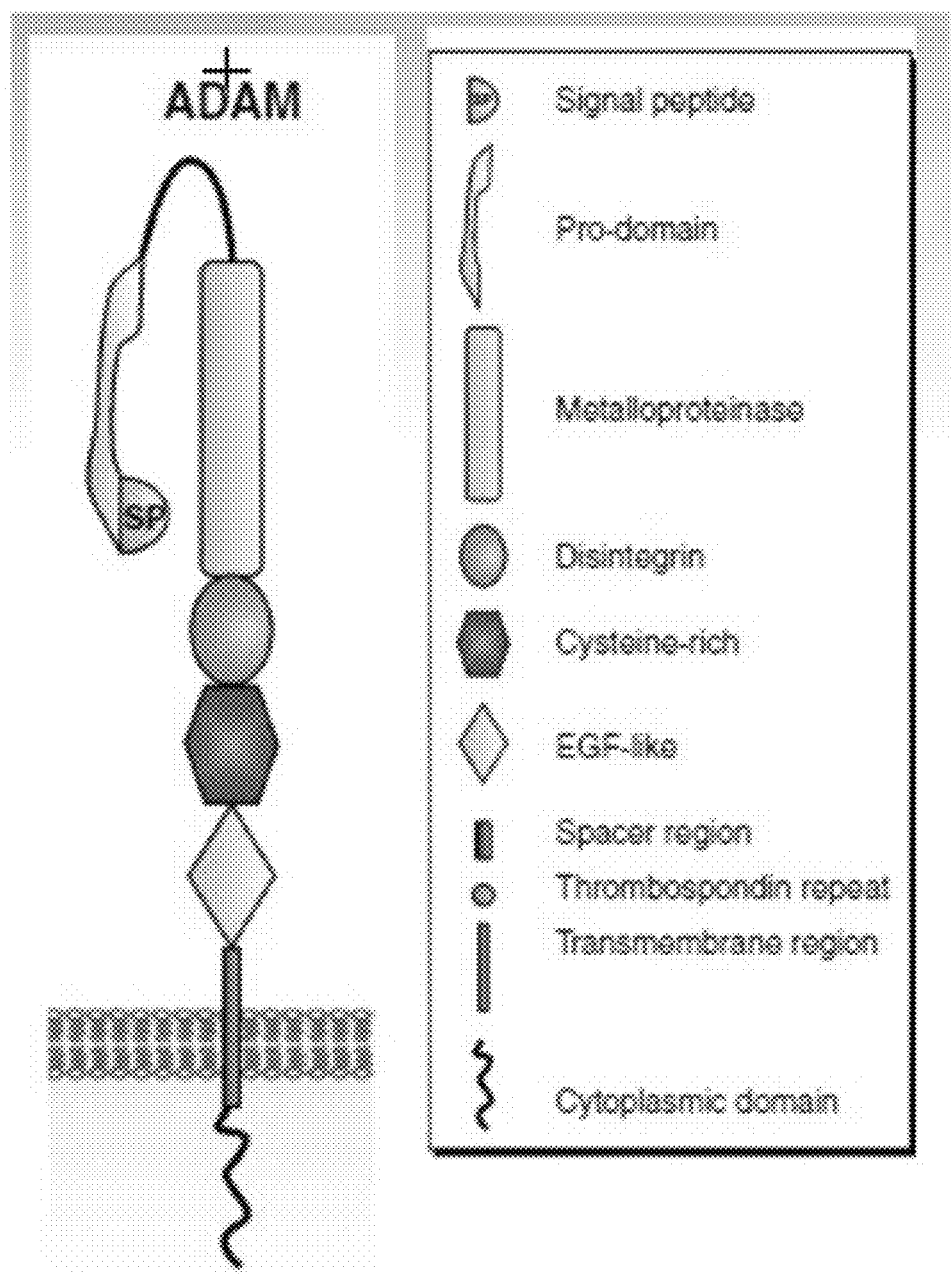
FIG. 7 shows the structure of ADAM30.
Figure 8:
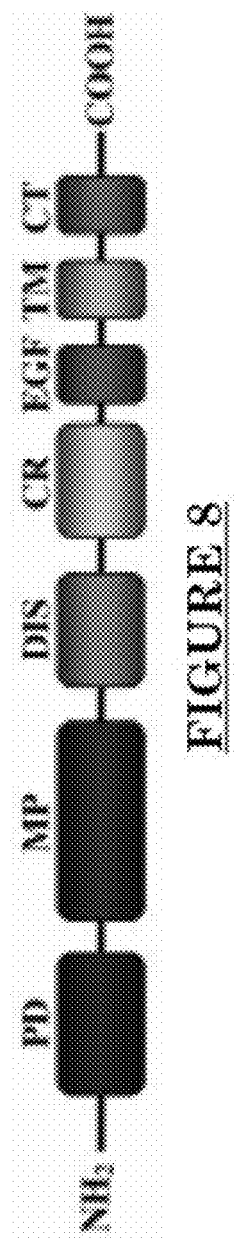
FIG. 8 shows an alternate structure of ADAM30.
Figure 9:
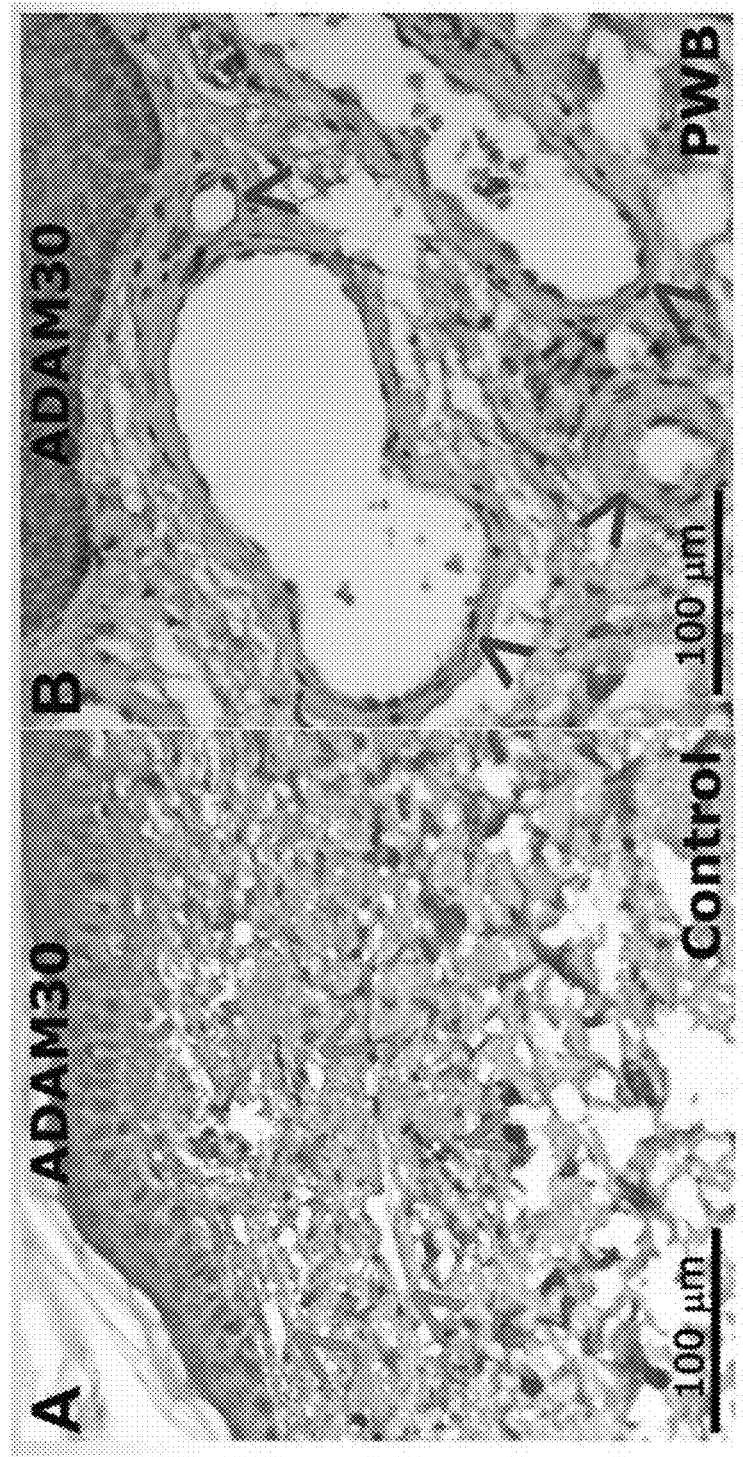
FIG. 9 shows ADAM30 overexpressions in PWS blood vessels in human skin.

ADAM 30 is one of the ADAMs (a disintegrin and metalloproteinase), which are a family of single-pass transmembrane and secreted metalloendopeptidases. The ADAM family is believed to a play a part in Alzheimer's disease, rheumatoid arthritis, atherosclerosis, asthma and cancer progression. ADAM30 plays a role in lysosomal Amyloid Precursor Protein (APP) processing, leading to APP degradation. FIG. 7 shows the structure of ADAM30. FIG. shows an alternate structure of ADAM30. FIG. 9 shows ADAM30 overexpressions in PWS blood vessels in human skin.

For example, the compositions of the present disclosure will have efficacy for treatment of patients suffering from the diseases and disorders disclosed above and/or other pathologies and disorders of the like. The polypeptides can be used as immunogens to produce antibodies specific for the disclosure, and as vaccines. They can also be used to screen for potential agonist and antagonist compounds. For example, a cDNA encoding ADAM30 may be useful in gene therapy, and ADAM30 may be useful when administered to a subject in need thereof. By way of non-limiting example, the compositions of the present disclosure will have efficacy for treatment of patients suffering from the diseases and disorders disclosed above and/or other pathologies and disorders of the like.

Figure 10:
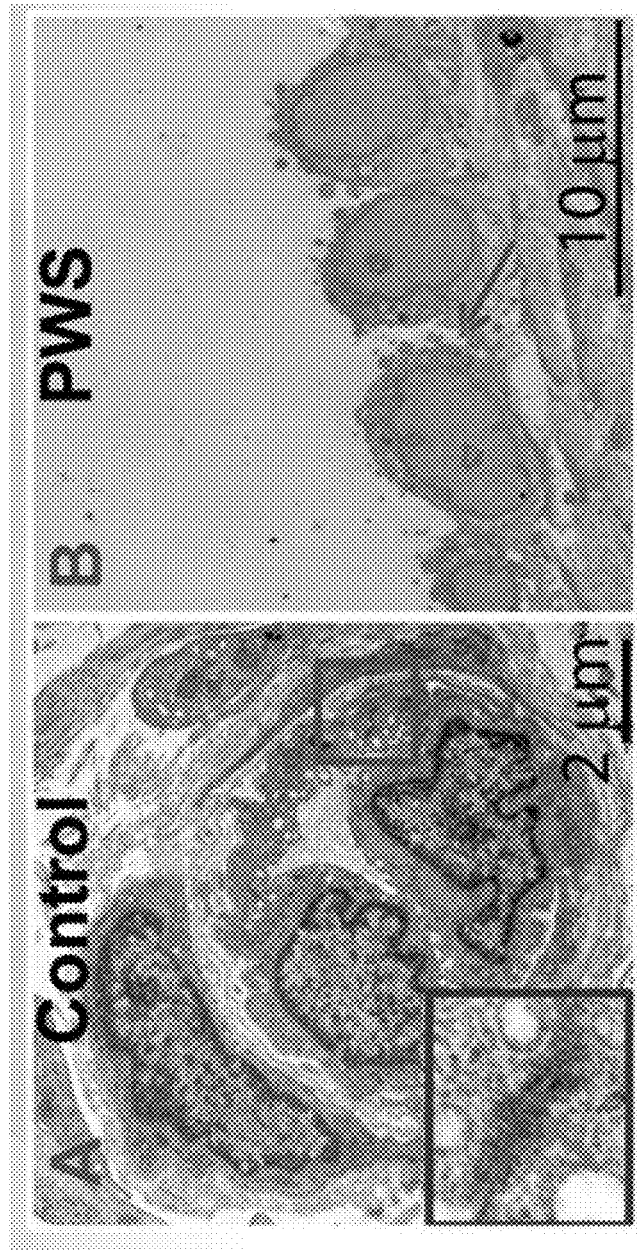
FIG. 10 shows Impairments of EC barriers in infantile PWS blood vessels Blue arrow: TJ from the area in red box.
Figure 11:
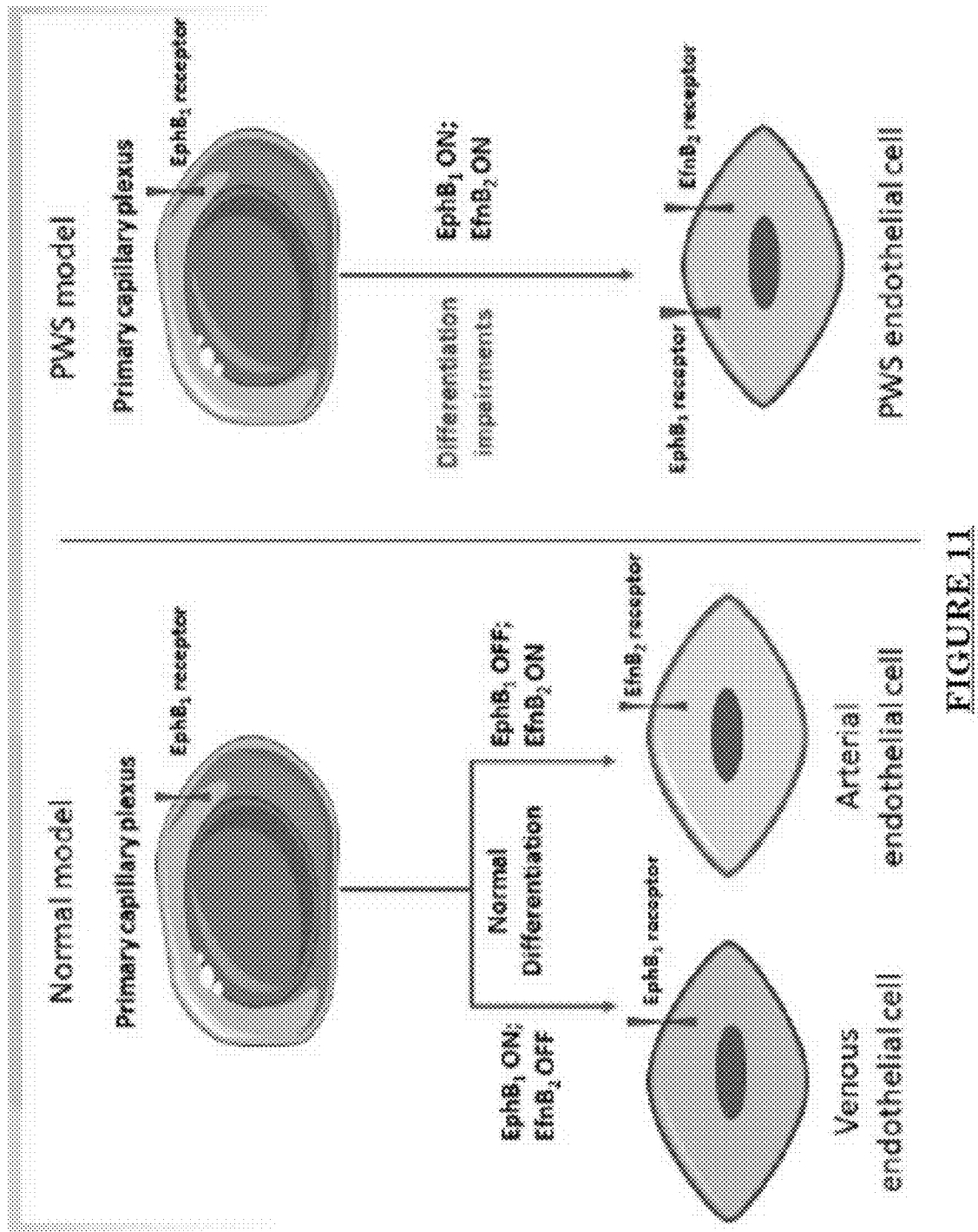
FIG. 11 shows EphB1 and EfnB2 co-express in the PWS ECs.
Figure 12:
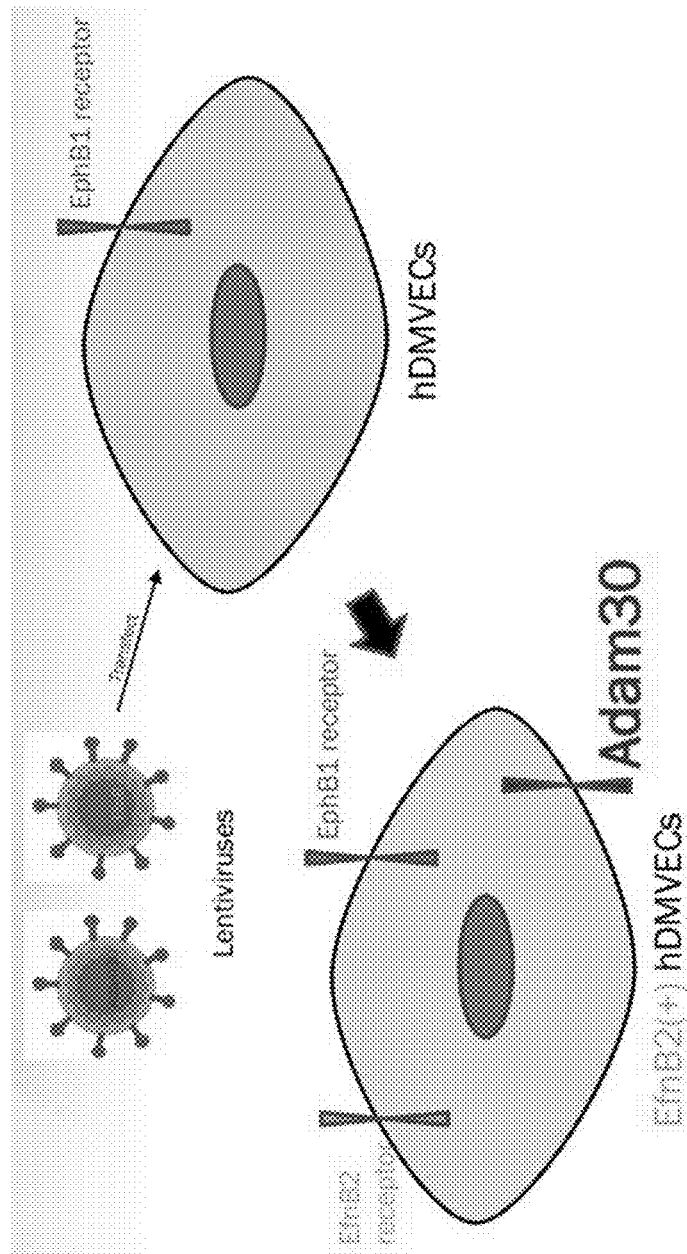
FIG. 12 shows ADAM30 and EfnB2 positive hDMVECs (human dermal microvascular endothelial cells).
Figure 13:
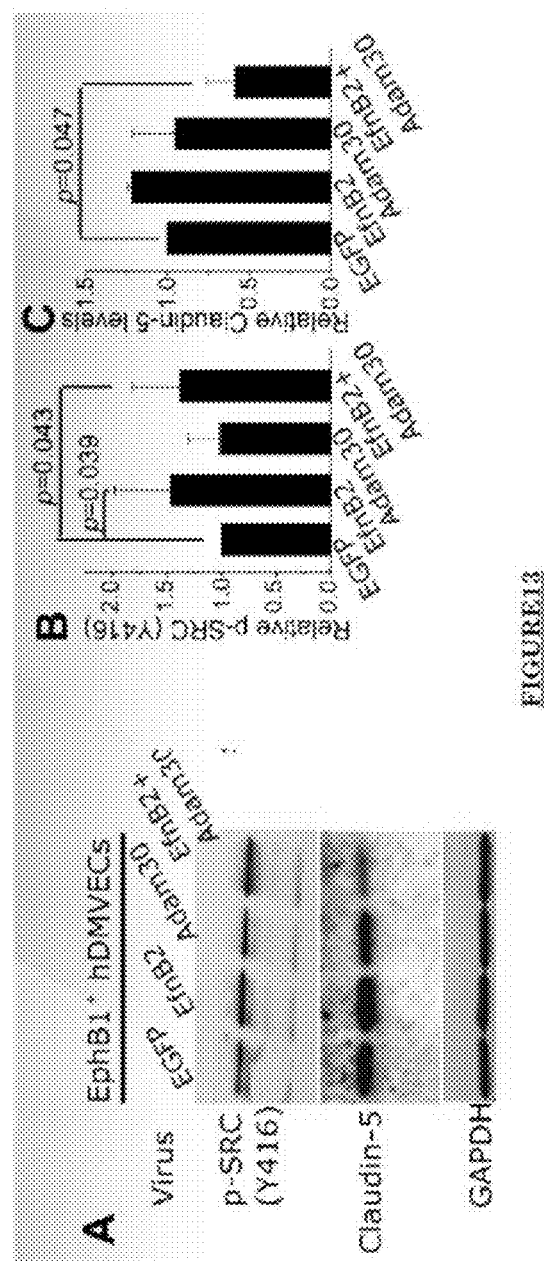
FIG. 13 shows ADAM30 overexpress decrease the Claudin5 level in hDMVECs.
Figure 14:
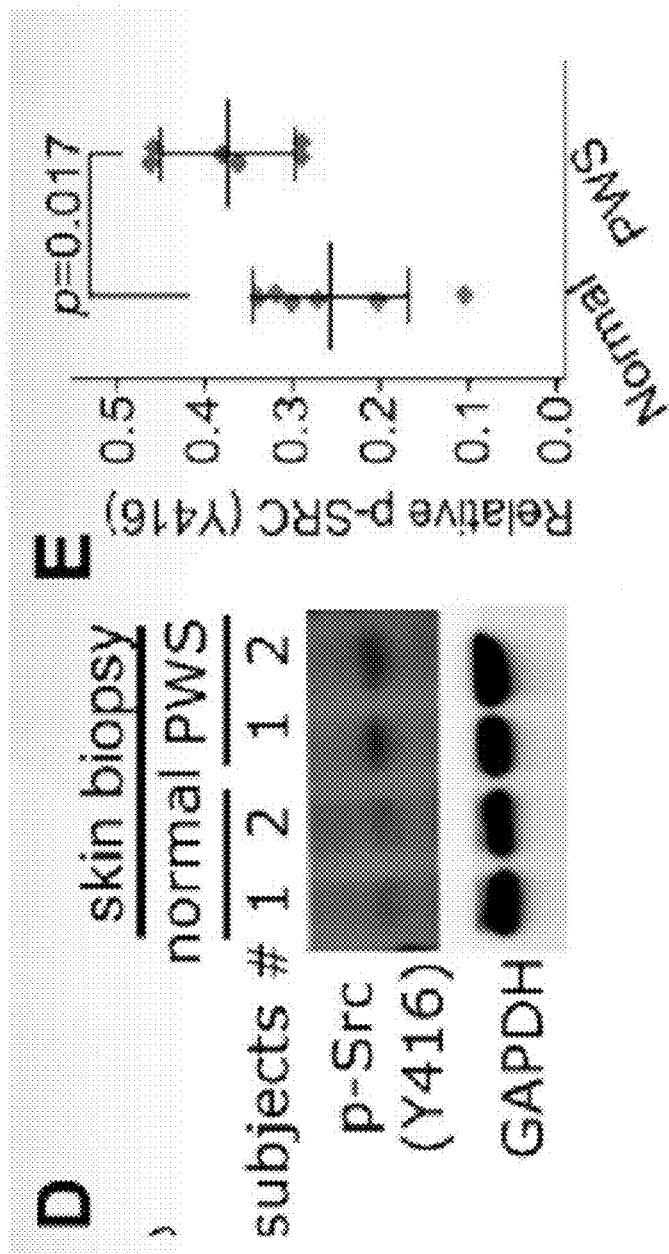
FIG. 14 shows activation of SRC in PWS skin.
Figure 16:
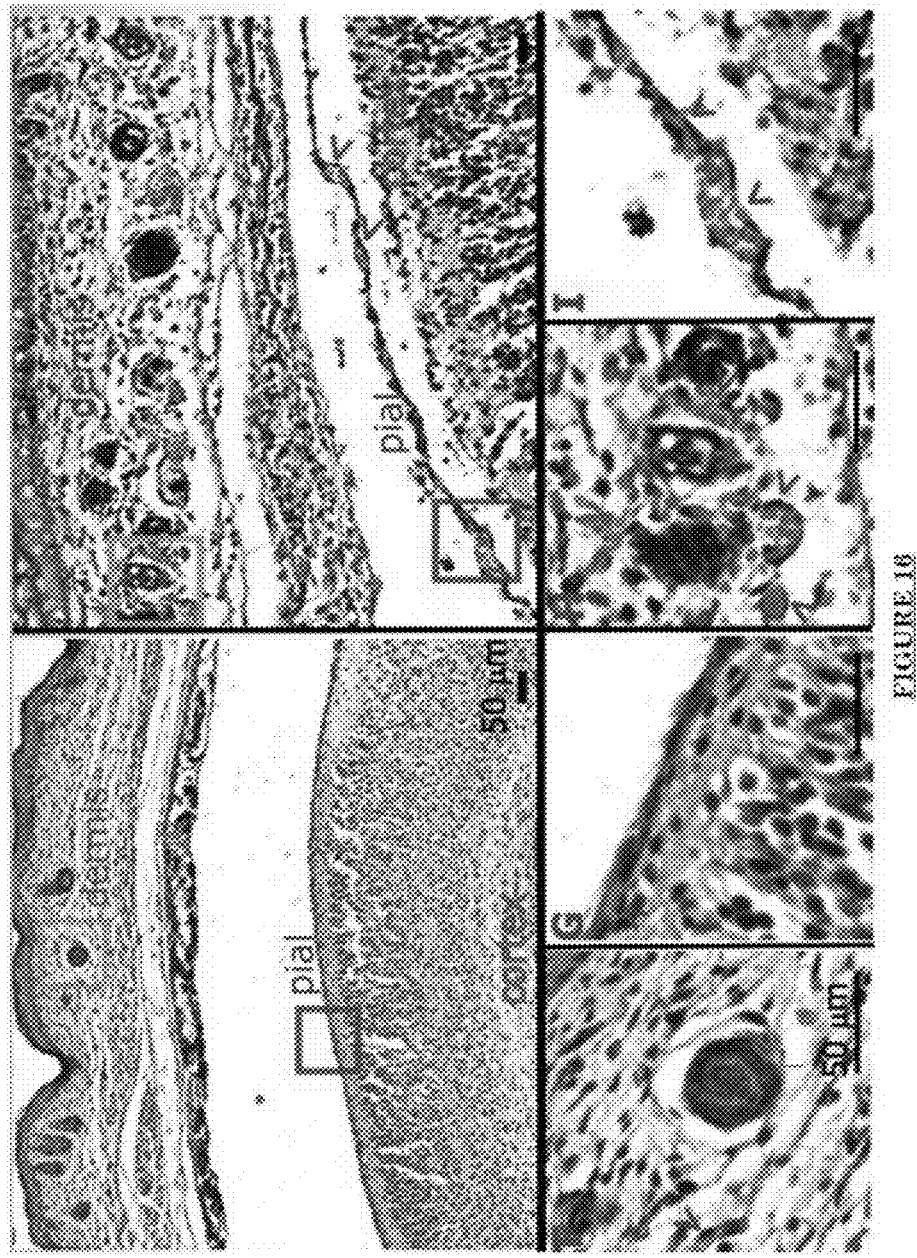
FIG. 16 shows ADAM30 mouse showing both dermal and leptomeningeal vascular malformations.
Figure 17:
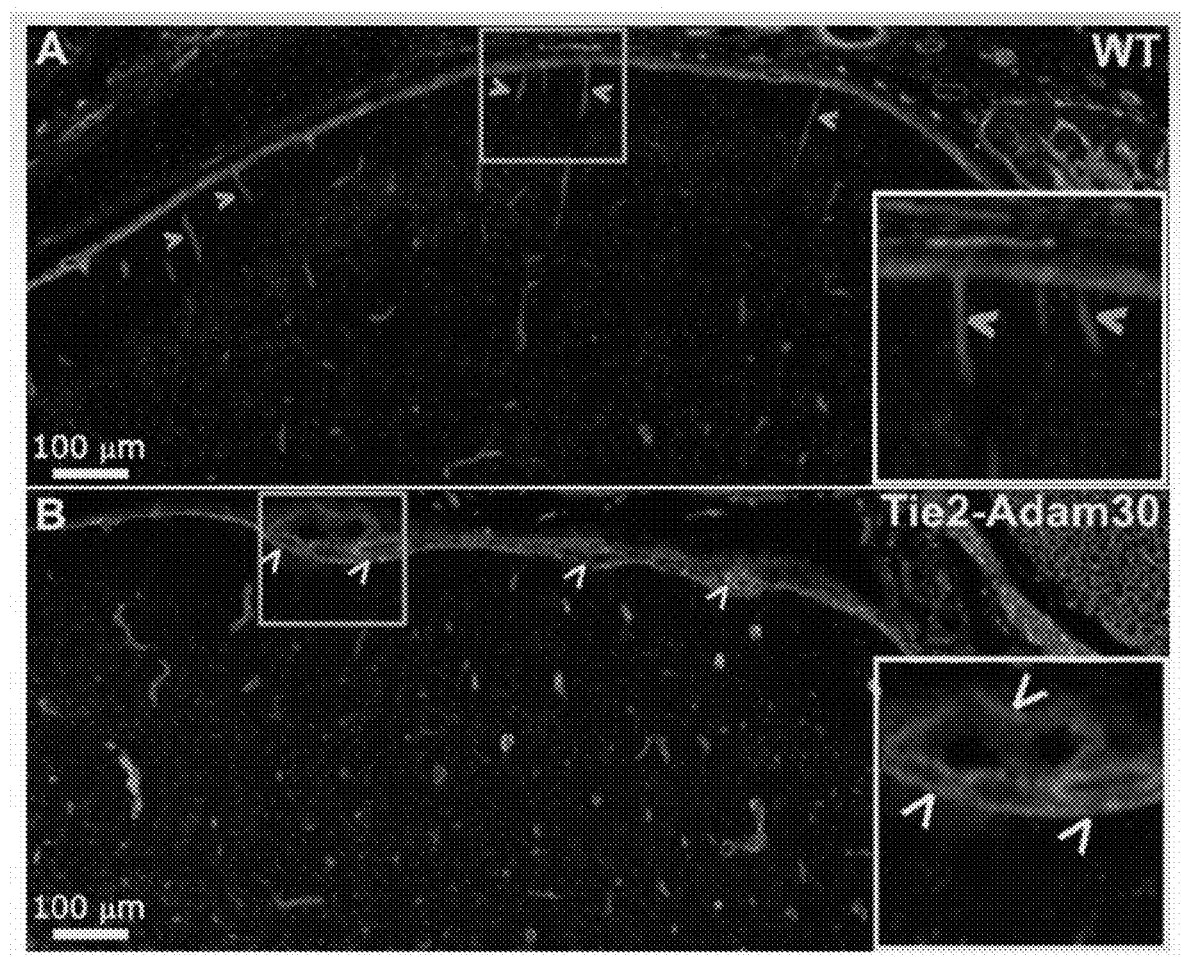
FIG. 17 shows Pial blood vessel dilation and loss of branching vessels into cortex in Adam30 Tg mouse.
Figure 18:
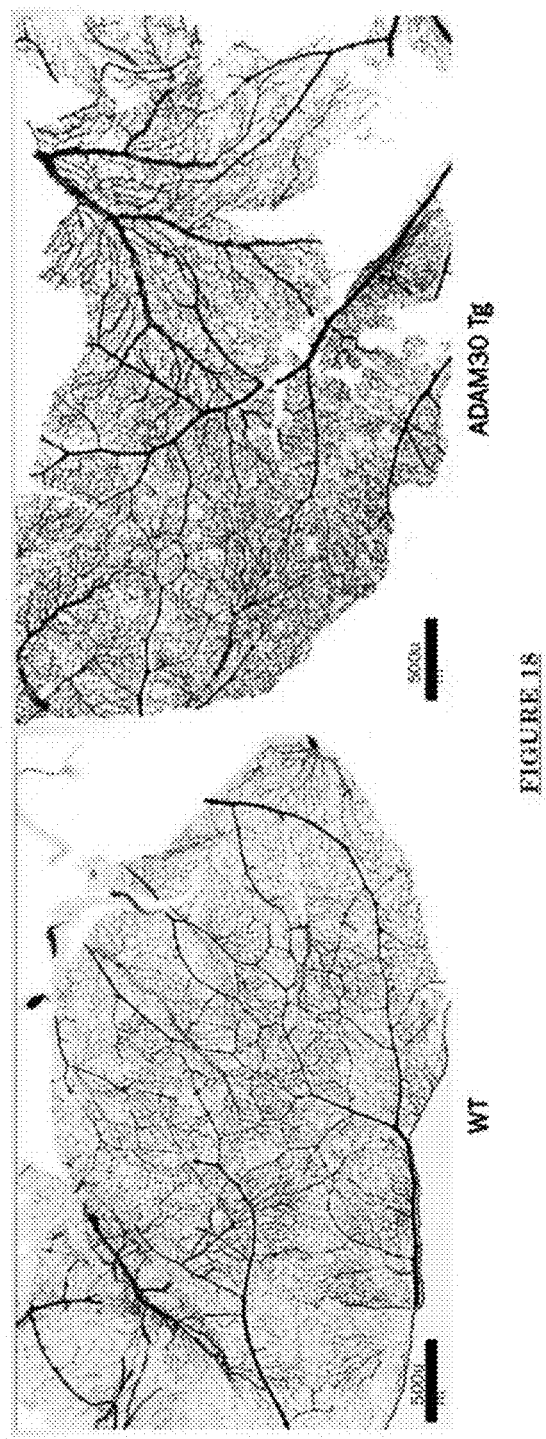
FIG. 18 shows dilation and increased densities of Pial blood vessels in Adam30 Tg mouse.
Figure 19:
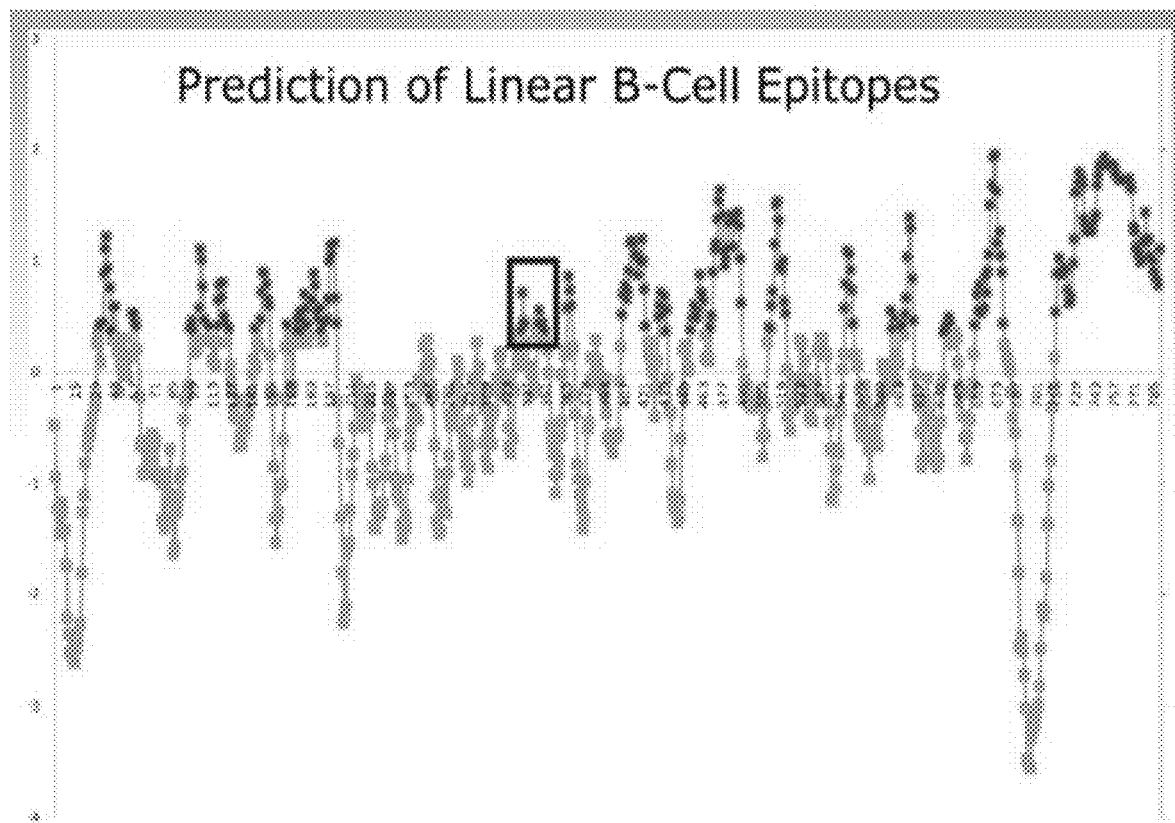
FIG. 19 shows anti-ADAM30 antibody development.
Figure 20:
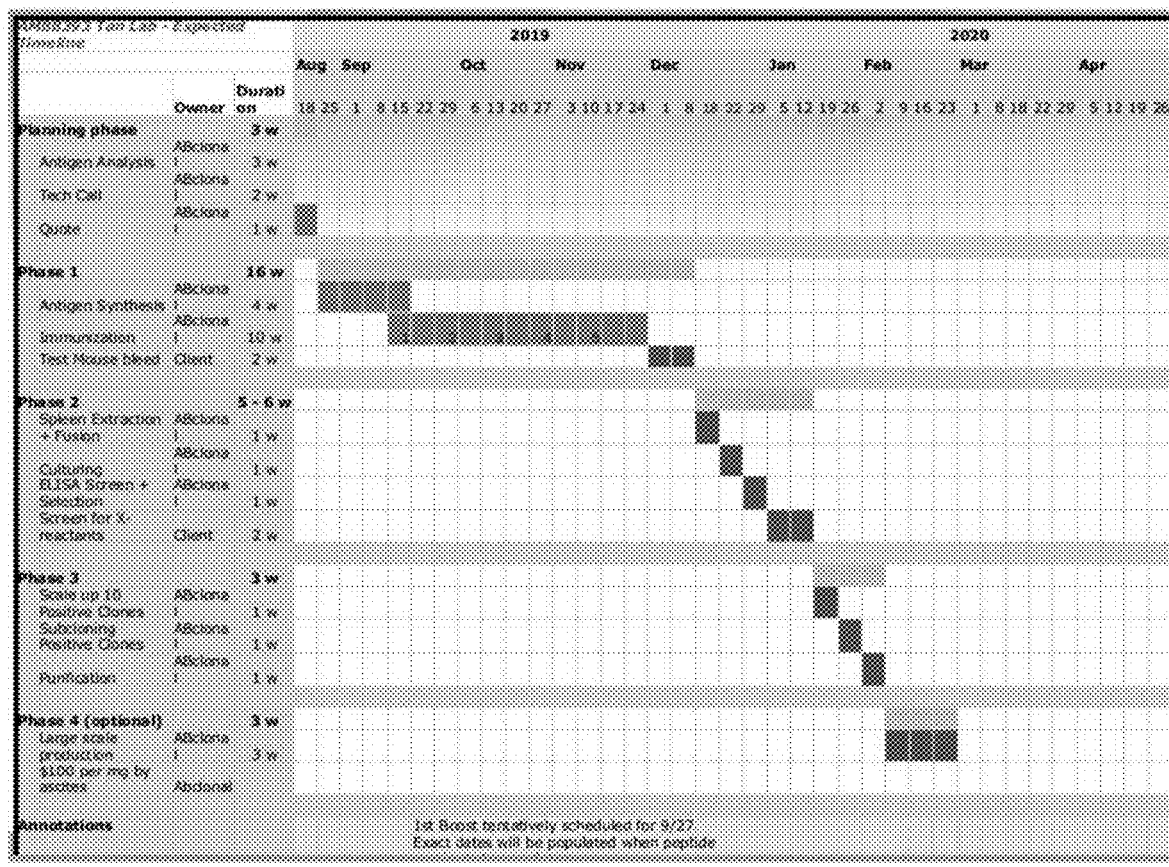
FIG. 20 shows agenda of anti-Adam30 antibody development.
Figure 21:
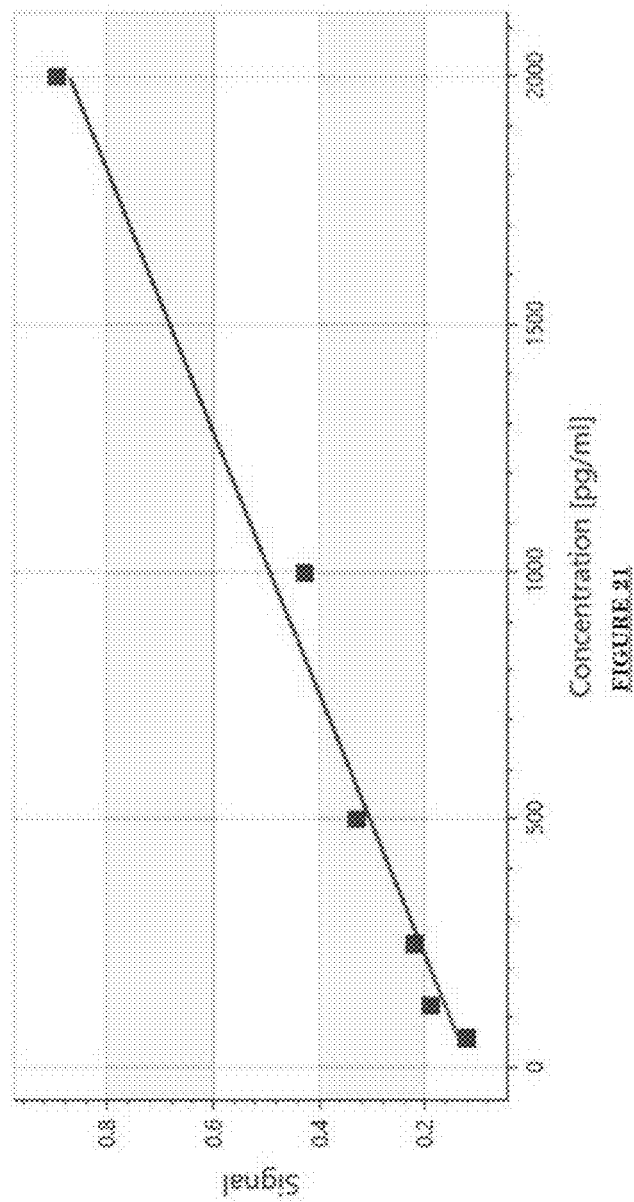
FIG. 21 shows a standard curve for ADAM30 ELISA.

FIG. 10 shows Impairments of EC barriers in infantile PWS blood vessels Blue arrow: TJ from the area in red box. FIG. 11 shows that EphB1 and EfnB2 co-express in the PWS ECs. FIG. 12 shows Adam30 and EfnB2 positive hDMVECs (human dermal microvascular endothelial cells). FIG. 13 shows ADAM30 overexpress decrease the Claudin5 level in hDMVECs. FIG. 14 shows activation of SRC in PWS skin. FIG. 15 shows a transgenic mouse sample with an overexpression of ADAM30 in ECs. FIG. 16 shows an ADAM30 mouse showing both dermal and leptomeningeal vascular malformations. FIG. 17 shows Pial blood vessel dilation and loss of branching vessels into cortex in Adam30 Tg mouse. FIG. 18 shows dilation and increased densities of Pial blood vessels in Adam30 Tg mouse. FIG. 19 shows anti-ADAM30 antibody development. Protein antigenicity analysis shows that the sequence (336-350 aa in the blue-boxed area) containing the predicted catalytic domain of ADAM30 meets the antigen criteria for immunization. The current disclosure is currently developing an antibody to neutralize the ADAM30 activity by targeting ADAM30 extracellular catalytic domain. FIG. 20 shows an agenda of anti-Adam30 antibody development. FIG. 21 shows a standard curve for ADAM30 ELISA. FIG. 22 shows ADAM30 levels in patients' serum (by ELISA).

Possible antibodies that may be employed against ADAM30 include LS-0540724, LS-C306091, LS-C107691, LS-C648837, LS-0502671, LS-C81425, LS-G88834, and/or LS-G61741 all available from LSBio. Further, other antibodies such as NBP1-86980, NBP1-62289, NBP1-62430, NBP1-69319, and 1100011085-M02 all available from Novus Biologicals, may be employed as well. Others include MA5-21251 from ThermoFisher Scientific.

This disclosure further includes a method for screening for a modulator of disorders or syndromes including, e.g., the diseases and disorders disclosed above and/or other pathologies and disorders of the like. The method includes contacting a test compound with a ADAM30 polypeptide and determining if the test compound binds to said ADAM30 polypeptide. Binding of the test compound to the ADAM30 polypeptide indicates the test compound is a modulator of activity, or of latency or predisposition to the aforementioned disorders or syndromes.

Also within the scope of the disclosure is a method for screening for a modulator of activity, or of latency or predisposition to disorders or syndromes including, e.g., the diseases and disorders disclosed above and/or other pathologies and disorders of the like by administering a test compound to a test animal at increased risk for the aforementioned disorders or syndromes. The test animal expresses a recombinant polypeptide encoded by a ADAM30 nucleic acid. Expression or activity of ADAM30 polypeptide is then measured in the test animal, as is expression or activity of the protein in a control animal which recombinantly-expresses ADAM30 polypeptide and is not at increased risk for the disorder or syndrome. Next, the expression of ADAM30 polypeptide in both the test animal and the control animal is compared. A change in the activity of ADAM30 polypeptide in the test animal relative to the control animal indicates the test compound is a modulator of latency of the disorder or syndrome.

In yet another aspect, the disclosure includes a method for determining the presence of or predisposition to a disease associated with altered levels of a ADAM30 polypeptide, a ADAM30 nucleic acid, or both, in a subject (e.g., a human subject). The method includes measuring the amount of the ADAM30 polypeptide in a test sample from the subject and comparing the amount of the polypeptide in the test sample to the amount of the ADAM30 polypeptide present in a control sample. An alteration in the level of the ADAM30 polypeptide in the test sample as compared to the control sample indicates the presence of or predisposition to a disease in the subject. Preferably, the predisposition includes, e.g., the diseases and disorders disclosed herein and/or other pathologies and disorders of the like. Also, the expression levels of the new polypeptides of the disclosure can be used in a method to screen for various cancers as well as to determine the stage of cancers.

In a further aspect, the disclosure includes a method of treating or preventing a pathological condition associated with a disorder in a mammal by administering to the subject a ADAM30 polypeptide, a ADAM30 nucleic acid, or a ADAM30-specific antibody to a subject (e.g., a human subject), in an amount sufficient to alleviate or prevent the pathological condition. In preferred embodiments, the disorder, includes, e.g., the diseases and disorders disclosed herein and/or other pathologies and disorders of the like.

Mutations can be introduced into SEQ ID NO: 1 by standard techniques, such as site-directed mutagenesis and PCR-mediated mutagenesis. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the ADAM30 protein is replaced with another amino acid residue from the same side chain family. Alternatively, in another embodiment, mutations can be introduced randomly along all or part of an ADAM30 coding sequence, such as by saturation mutagenesis, and the resultant mutants can be screened for ADAM30 biological activity to identify mutants that retain activity. Following mutagenesis SEQ ID NO: 1, the encoded protein can be expressed by any recombinant technology known in the art and the activity of the protein can be determined.

Anti-ADAM30 Antibodies

Also included in the disclosure are antibodies to ADAM30 proteins, or fragments of ADAM30 proteins. The term "antibody" as used herein refers to immunoglobulin molecules and immunologically active portions of immunoglobulin (Ig) molecules, i.e., molecules that contain an antigen binding site that specifically binds (immunoreacts with) an antigen. Such antibodies include, but are not limited to, polyclonal, monoclonal, chimeric, single chain, Fab, Fab, and F(ab')2 fragments, and an Fab expression library. In general, an antibody molecule obtained from humans relates to any of the classes IgG, IgM, IgA, IgE and IgD, which differ from one another by the nature of the heavy chain present in the molecule. Certain classes have subclasses as well, such as IgG1, IgG2, and others. Furthermore, in humans, the light chain may be a kappa chain or a lambda chain. Reference herein to antibodies includes a reference to all such classes, subclasses and types of human antibody species.

An isolated ADAM30-related protein of the disclosure may be intended to serve as an antigen, or a portion or fragment thereof, and additionally can be used as an immunogen to generate antibodies that immunospecifically bind the antigen, using standard techniques for polyclonal and monoclonal antibody preparation. The full-length protein can be used or, alternatively, the disclosure provides antigenic peptide fragments of the antigen for use as immunogens. An antigenic peptide fragment comprises at least 6 amino acid residues of the amino acid sequence of the full length protein and encompasses an epitope thereof such that an antibody raised against the peptide forms a specific immune complex with the full length protein or with any fragment that contains the epitope. Preferably, the antigenic peptide comprises at least 10 amino acid residues, or at least 15 amino acid residues, or at least 20 amino acid residues, or at least 30 amino acid residues. Preferred epitopes encompassed by the antigenic peptide are regions of the protein that are located on its surface; commonly these are hydrophilic regions.

In certain embodiments of the disclosure, at least one epitope encompassed by the antigenic peptide is a region of ADAM30-related protein that is located on the surface of the protein, e.g., a hydrophilic region. A hydrophobicity analysis of the human ADAM30-related protein sequence will indicate which regions of an ADAM30-related protein are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each of which is incorporated herein by reference in its entirety. Antibodies that are specific for one or more domains within an antigenic protein, or derivatives, fragments, analogs or homologs thereof, are also provided herein.

A protein of the disclosure, or a derivative, fragment, analog, homolog or ortholog thereof, may be utilized as an immunogen in the generation of antibodies that immunospecifically bind these protein components.

Various procedures known within the art may be used for the production of polyclonal or monoclonal antibodies directed against a protein of the disclosure, or against derivatives, fragments, analogs homologs or orthologs thereof (see, for example, Antibodies: A Laboratory Manual, Harlow and Lane, 1988, Cold Spring Harbor Laboratory Press, Cold Spring Harbor, N.Y., incorporated herein by reference). Some of these antibodies are discussed below.

Polyclonal Antibodies

For the production of polyclonal antibodies, various suitable host animals (e.g., rabbit, goat, mouse or other mammal) may be immunized by one or more injections with the native protein, a synthetic variant thereof, or a derivative of the foregoing. An appropriate immunogenic preparation can contain, for example, the naturally occurring immunogenic protein, a chemically synthesized polypeptide representing the immunogenic protein, or a recombinantly expressed immunogenic protein. Furthermore, the protein may be conjugated to a second protein known to be immunogenic in the mammal being immunized. Examples of such immunogenic proteins include but are not limited to keyhole limpet hemocyanin, serum albumin, bovine thyroglobulin, and soybean trypsin inhibitor. The preparation can further include an adjuvant. Various adjuvants used to increase the immunological response include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.), adjuvants usable in humans such as Bacille Calmette-Guerin and *Corynebacterium parvum*, or similar immunostimulatory agents. Additional examples of adjuvants which can be employed include MPL-TDM adjuvant (monophosphoryl Lipid A, synthetic trehalose dicorynomycolate).

The polyclonal antibody molecules directed against the immunogenic protein can be isolated from the mammal (e.g., from the blood) and further purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

Monoclonal Antibodies

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs thus contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, MONOCLONAL ANTIBODIES: PRINCIPLES AND PRACTICE, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies (Kozbor, J. Immunol., 133:3001 (1984); Brodeur et al, MONOCLONAL ANTIBODY PRODUCTION TECHNIQUES AND APPLICATIONS, Marcel Dekker, Inc., New York, (1987) pp. 51-63).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Preferably, antibodies having a high degree of specificity and a high binding affinity for the target antigen are isolated.

After the desired hybridoma cells are identified, the clones can be subcloned by limiting dilution procedures and grown by standard methods. Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

The monoclonal antibodies can also be made by recombinant DNA methods, such as those described in U.S. Pat. No. 4,816,567. DNA encoding the monoclonal antibodies of the disclosure can be readily isolated and sequenced using conventional procedures (e.g., by using oligonucleotide probes that are capable of binding specifically to genes encoding the heavy and light chains of murine antibodies). The hybridoma cells of the disclosure serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the disclosure, or can be substituted for the variable domains of one antigen-combining site of an antibody of the disclosure to create a chimeric bivalent antibody.

Humanized Antibodies

The antibodies directed against the protein antigens of the disclosure can further comprise humanized antibodies or human antibodies. These antibodies are suitable for administration to humans without engendering an immune response by the human against the administered immunoglobulin. Humanized forms of antibodies are chimeric immunoglobulins, immunoglobulin chains or fragments thereof (such as Fv, Fab, Fab', F(ab')2 or other antigen-binding subsequences of antibodies) that are principally comprised of the sequence of a human immunoglobulin, and contain minimal sequence derived from a non-human immunoglobulin. Humanization can be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. (See also U.S. Pat. No. 5,225,539.) In some instances, Fv framework residues of the human immunoglobulin are replaced by corresponding non-human residues. Humanized antibodies can also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the framework regions are those of a human immunoglobulin consensus sequence. The humanized antibody optimally also will comprise at least a portion of an immunoglobulin constant region (Fc), typically that of a human immunoglobulin (Jones et al., 1986; Riechmann et al., 1988; and Presta, Curr. Op. Struct. Biol., 2:593-596 (1992)).

Human Antibodies

Fully human antibodies relate to antibody molecules in which essentially the entire sequences of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present disclosure and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouselm as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

An example of a method of producing a nonhuman host, exemplified as a mouse, lacking expression of an endogenous immunoglobulin heavy chain is disclosed in U.S. Pat. No. 5,939,598. It can be obtained by a method including deleting the J segment genes from at least one endogenous heavy chain locus in an embryonic stem cell to prevent rearrangement of the locus and to prevent formation of a transcript of a rearranged immunoglobulin heavy chain locus, the deletion being effected by a targeting vector containing a gene encoding a selectable marker; and producing from the embryonic stem cell a transgenic mouse whose somatic and germ cells contain the gene encoding the selectable marker.

A method for producing an antibody of interest, such as a human antibody, is disclosed in U.S. Pat. No. 5,916,771. It includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

Fab Fragments and Single Chain Antibodies

According to the disclosure, techniques can be adapted for the production of single-chain antibodies specific to an antigenic protein of the disclosure (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab)2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the disclosure. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., 1991 EMBO J., 10:3655-3659.

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CM, and $CH_3$ regions. It is preferred to have the first heavy-chain constant region (CHO containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the $CH_3$ region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from *E. coli* and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VII and VL domains of one fragment are forced to pair with the complementary VL and VII domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994).

Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the disclosure. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (Fc&ggr;R), such as Fc&ggr; RI (CD64), Fc&ggr;RII (CD32) and Fc&ggr;RIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA. Another bispecific antibody of interest binds the protein antigen described herein and further binds tissue factor (TF).

Heteroconjugate Antibodies

Heteroconjugate antibodies are also within the scope of the present disclosure. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Effector Function Engineering

It can be desirable to modify the antibody of the disclosure with respect to effector function, so as to enhance, e.g., the effectiveness of the antibody in treating cancer. For example, cysteine residue(s) can be introduced into the Fc region, thereby allowing interchain disulfide bond formation in this region. The homothmeric antibody thus generated can have improved internalization capability and/or increased complement-mediated cell killing and antibody-dependent cellular cytotoxicity (ADCC). See Caron et al., J. Exp Med., 176: 1191-1195 (1992) and Shopes, J. Immunol., 148: 2918-2922 (1992). Homodimeric antibodies with enhanced anti-tumor activity can also be prepared using heterobifunctional cross-linkers as described in Wolff et al. Cancer Research, 53: 2560-2565 (1993). Alternatively, an antibody can be engineered that has dual Fc regions and can thereby have enhanced complement lysis and ADCC capabilities. See Stevenson et al., Anti-Cancer Drug Design, 3: 219-230 (1989).

Immunoconjugates

The disclosure also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (ie., a radioconjugate).

Chemotherapeutic agents useful in the generation of such immunoconjugates have been described above. Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites* ford ii proteins, dianthin proteins, *Phytolaca americana* proteins (PAPI, PAPII, and PAP-S), momordica *charantia* inhibitor, curcin, crotin, sap aonaria *officinalis* inhibitor, gelonin, mitogellin, restrictocin, phenomycin, enomycin, and the tricothecenes. A variety of radionuclides are available for the production of radioconjugated antibodies. Examples include 212Bi, 131I, 131In, 90Y, and 186Re.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" (such streptavidin) for utilization in tumor pretargeting wherein the antibody-receptor conjugate is administered to the patient, followed by removal of unbound conjugate from the circulation using a clearing agent and then administration of a "ligand" (e.g., avidin) that is in turn conjugated to a cytotoxic agent.

In one embodiment, methods for the screening of antibodies that possess the desired specificity include, but are not limited to, enzyme-linked immunosorbent assay (ELISA) and other immunologically-mediated techniques known within the art. In a specific embodiment, selection of antibodies that are specific to a particular domain of an ADAM30 protein is facilitated by generation of hybridomas that bind to the fragment of an ADAM30 protein possessing such a domain. Thus, antibodies that are specific for a desired domain within an ADAM30 protein, or derivatives, fragments, analogs or homologs thereof, are also provided herein.

Anti-ADAM30 antibodies may be used in methods known within the art relating to the localization and/or quantitation of an ADAM30 protein (e.g., for use in measuring levels of the ADAM30 protein within appropriate physiological samples, for use in diagnostic methods, for use in imaging the protein, and the like). In a given embodiment, antibodies for ADAM30 proteins, or derivatives, fragments, analogs or homologs thereof, that contain the antibody derived binding domain, are utilized as pharmacologically-active compounds (hereinafter "Therapeutics").

An anti-ADAM30 antibody (e.g., monoclonal antibody) can be used to isolate an ADAM30 polypeptide by standard techniques, such as affinity chromatography or immunoprecipitation. An anti-ADAM30 antibody can facilitate the purification of natural ADAM30 polypeptide from cells and of recombinantly-produced ADAM30 polypeptide expressed in host cells. Moreover, an anti-ADAM30 antibody can be used to detect ADAM30 protein (e.g., in a cellular lysate or cell supernatant) in order to evaluate the abundance and pattern of expression of the ADAM30 protein. Anti-ADAM30 antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, &bgr;-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include 125I, 131I, 35S or 3H.

ADAM30 Recombinant Expression Vectors and Host Cells

Another aspect of the disclosure pertains to vectors, preferably expression vectors, containing a nucleic acid encoding an ADAM30 protein, or derivatives, fragments, analogs or homologs thereof. As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the disclosure is intended to include such other forms of expression vectors, such as viral vectors (e.g. replication defective retroviruses, adenoviruses and adeno-associated viruses), which serve equivalent functions.

The recombinant expression vectors of the disclosure comprise a nucleic acid of the disclosure in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to includes promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the disclosure can be introduced into host cells to thereby produce proteins or peptides, including fusion proteins or peptides, encoded by nucleic acids as described herein (e.g., ADAM30 proteins, mutant forms of ADAM30 proteins, fusion proteins, etc.).

The recombinant expression vectors of the disclosure can be designed for expression of ADAM30 proteins in prokaryotic or eukaryotic cells. For example, ADAM30 proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 3140), pMAL (New England Biolabs, Beverly, Mass.) and pRIT5 (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the disclosure can be carried out by standard DNA synthesis techniques.

In another embodiment, the ADAM30 expression vector is a yeast expression vector. Examples of vectors for expression in yeast *Saccharomyces cerevisiae* include pYepSec1 (Baldari, et al., 1987. EMBO J. 6: 229-234), pMFa (Kurjan and Herskowitz, 1982. Cell 30: 933-943), pJRY88 (Schultz et al., 1987. Gene 54: 113-123), pYES2 (Invitrogen Corporation, San Diego, Calif.), and picZ (InVitrogen Corp, San Diego, Calif.).

Alternatively, ADAM30 can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the disclosure is expressed in mammalian cells using a mammalian expression vector. Examples of mammalian expression vectors include pCDM8 (Seed, 1987. Nature 329: 840) and pMT2PC (Kaufman, et al., 1987. EMBO J. 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et a., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the &agr;-fetoprotein promoter (Campes and Tilghman, 1989. Genes Dev. 3: 537-546).

The disclosure further provides a recombinant expression vector comprising a DNA molecule of the disclosure cloned into the expression vector in an antisense orientation. That is, the DNA molecule is operatively-linked to a regulatory sequence in a manner that allows for expression (by transcription of the DNA molecule) of an RNA molecule that is antisense to ADAM30 mRNA. Regulatory sequences operatively linked to a nucleic acid cloned in the antisense orientation can be chosen that direct the continuous expression of the antisense RNA molecule in a variety of cell types, for instance viral promoters and/or enhancers, or regulatory sequences can be chosen that direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see, e.g., Weintraub, et al., "Antisense RNA as a molecular tool for genetic analysis," Reviews-Trends in Genetics, Vol. 1(1) 1986.

Another aspect of the disclosure pertains to host cells into which a recombinant expression vector of the disclosure has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, ADAM30 protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAF-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding ADAM30 or can be introduced on a separate vector. Cells stably transfected with the introduced nucleic acid can be identified by drug selection (e.g., cells that have incorporated the selectable marker gene will survive, while the other cells die).

A host cell of the disclosure, such as a prokaryotic or eukaryotic host cell in culture, can be used to produce (i.e., express) ADAM30 protein. Accordingly, the disclosure further provides methods for producing ADAM30 protein using the host cells of the disclosure. In one embodiment, the method comprises culturing the host cell of disclosure (into which a recombinant expression vector encoding ADAM30 protein has been introduced) in a suitable medium such that ADAM30 protein is produced. In another embodiment, the method further comprises isolating ADAM30 protein from the medium or the host cell.

Transgenic ADAM30 Animals

The host cells of the disclosure can also be used to produce non-human transgenic animals. For example, in one embodiment, a host cell of the disclosure is a fertilized oocyte or an embryonic stem cell into which ADAM30 protein-coding sequences have been introduced. Such host cells can then be used to create non-human transgenic animals in which exogenous ADAM30 sequences have been introduced into their genome or homologous recombinant animals in which endogenous ADAM30 sequences have been altered. Such animals are useful for studying the function and/or activity of ADAM30 protein and for identifying and/or evaluating modulators of ADAM30 protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous ADAM30 gene has been altered by homologous recombination between the endogenous gene and an exogenous DNA molecule introduced into a cell of the animal, e.g., an embryonic cell of the animal, prior to development of the animal.

A transgenic animal of the disclosure can be created by introducing ADAM30-encoding nucleic acid into the male pronuclei of a fertilized oocyte (e.g., by microinjection, retroviral infection) and allowing the oocyte to develop in a pseudopregnant female foster animal. The human ADAM30 cDNA sequences SEQ ID NO: 1 can be introduced as a transgene into the genome of a non-human animal. Alternatively, a non-human homologue of the human ADAM30 gene, such as a mouse ADAM30 gene, can be isolated based on hybridization to the human ADAM30 cDNA (described further supra) and used as a transgene. Intronic sequences and polyadenylation signals can also be included in the transgene to increase the efficiency of expression of the transgene. A tissue-specific regulatory sequencers) can be operably-linked to the ADAM30 transgene to direct expression of ADAM30 protein to particular cells. Methods for generating transgenic animals via embryo manipulation and microinjection, particularly animals such as mice, have become conventional in the art and are described, for example, in U.S. Pat. Nos. 4,736,866; 4,870,009; and 4,873,191; and Hogan, 1986. In: MANIPULATING THE MOUSE EMBRYO, Cold Spring Harbor Laboratory Press, Cold Spring Harbor, N.Y. Similar methods are used for production of other transgenic animals. A transgenic founder animal can be identified based upon the presence of the ADAM30 transgene in its genome and/or expression of ADAM30 mRNA in tissues or cells of the animals. A transgenic founder animal can then be used to breed additional animals carrying the transgene. Moreover, transgenic animals carrying a transgene-encoding ADAM30 protein can further be bred to other transgenic animals carrying other transgenes.

To create a homologous recombinant animal, a vector is prepared which contains at least a portion of an ADAM30 gene into which a deletion, addition or substitution has been introduced to thereby alter, e.g., functionally disrupt, the ADAM30 gene. The ADAM30 gene can be a human gene (e.g., the cDNA of SEQ ID NO: 1), but more preferably, is a non-human homologue of a human ADAM30 gene. For example, a mouse homologue of human ADAM30 gene of SEQ ID NO: 1 can be used to construct a homologous recombination vector suitable for altering an endogenous ADAM30 gene in the mouse genome. In one embodiment, the vector is designed such that, upon homologous recombination, the endogenous ADAM30 gene is functionally disrupted (ie., no longer encodes a functional protein; also referred to as a "knock out" vector).

Alternatively, the vector can be designed such that, upon homologous recombination, the endogenous ADAM30 gene is mutated or otherwise altered but still encodes functional protein (e.g., the upstream regulatory region can be altered to thereby alter the expression of the endogenous ADAM30 protein). In the homologous recombination vector, the altered portion of the ADAM30 gene is flanked at its 5'- and 3'-termini by additional nucleic acid of the ADAM30 gene to allow for homologous recombination to occur between the exogenous ADAM30 gene carried by the vector and an endogenous ADAM30 gene in an embryonic stem cell. The additional flanking ADAM30 nucleic acid is of sufficient length for successful homologous recombination with the endogenous gene. Typically, several kilobases of flanking DNA (both at the 5'- and 3'-termini) are included in the vector. See, e.g., Thomas, et al., 1987. Cell 51: 503 for a description of homologous recombination vectors. The vector is ten introduced into an embryonic stem cell line (e.g., by electroporation) and cells in which the introduced ADAM30 gene has homologously-recombined with the endogenous ADAM30 gene are selected.

See, e.g., Li, et al., 1992. Cell 69: 915. The selected cells are then injected into a blastocyst of an animal (e.g., a mouse) to form aggregation chimeras. See, e.g., Bradley, 1987. In: TERATOCARCINOMAS AND EMBRYONIC STEM CELLS: A PRACTICAL APPROACH, Robertson, ed. IRL, Oxford, pp. 113-152. A chimeric embryo can then be implanted into a suitable pseudopregnant female foster animal and the embryo brought to term. Progeny harboring the homologously-recombined DNA in their germ cells can be used to breed animals in which all cells of the animal contain the homologously-recombined DNA by gernmine transmission of the transgene. Methods for constructing homologous recombination vectors and homologous recombinant animals are described further in Bradley, 1991. Curr. Opin. Biotechnol. 2: 823-829; PCT International Publication Nos.: WO 90/11354; WO 91/01140; WO 92/0968; and WO 93/04169.

In another embodiment, transgenic non-humans animals can be produced that contain selected systems that allow for regulated expression of the transgene. One example of such a system is the cre/loxP recombinase system of bacteriophage P1. For a description of the cre/loxP recombinase system, See, e.g., Lakso, et al., 1992. Proc. Natl. Acad. Sci. USA 89: 6232-6236. Another example of a recombinase system is the FLP recombinase system of *Saccharomyces cerevisiae*. See, O'Gorman, et al., 1991. Science 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, et al., 1997. Nature 385: 810-813. In brief, a cell (e.g., a somatic cell) from the transgenic animal can be isolated and induced to exit the growth cycle and enter GO phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyte and then transferred to pseudopregnant female foster animal. The offspring borne of this female foster animal will be a clone of the animal from which the cell (e.g., the somatic cell) is isolated.

Pharmaceutical Compositions

The ADAM30 nucleic acid molecules, ADAM30 proteins, and anti-ADAM30 antibodies (also referred to herein as "active compounds") of the disclosure, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the disclosure is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., an ADAM30 protein or anti-ADAM30 antibody) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; id a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the disclosure are dictated by and directly dependent on the unique characteristics of the active compound and the particular therapeutic effect to be achieved, and the limitations inherent in the art of compounding such an active compound for the treatment of individuals.

The nucleic acid molecules of the disclosure can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natr. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system.

The pharmaceutical compositions can be included in a container, pack, or dispenser together with instructions for administration.

Screening and Detection Methods

The isolated nucleic acid molecules of the disclosure can be used to express ADAM30 protein (e.g., via a recombinant expression vector in a host cell in gene therapy applications), to detect ADAM30 mRNA (e.g., in a biological sample) or a genetic lesion in an ADAM30 gene, and to modulate ADAM30 activity, as described further, below. In addition, the ADAM30 proteins can be used to screen drugs or compounds that modulate the ADAM30 protein activity or expression as well as to treat disorders characterized by insufficient or excessive production of ADAM30 protein or production of ADAM30 protein forms that have decreased or aberrant activity compared to ADAM30 wild-type protein; and various cancers. In addition, the anti-ADAM30 antibodies of the disclosure can be used to detect and isolate ADAM30 proteins and modulate ADAM30 activity.

The disclosure further pertains to novel agents identified by the screening assays described herein and uses thereof for treatments as described, supra.

Screening Assays

The disclosure provides a method (also referred to herein as a "screening assay") for identifying modulators, i.e., candidate or test compounds or agents (e.g., peptides, peptidomimetics, small molecules or other drugs) that bind to ADAM30 proteins or have a stimulatory or inhibitory effect on, e.g., ADAM30 protein expression or ADAM30 protein activity. The disclosure also includes compounds identified in the screening assays described herein.

In one embodiment, the disclosure provides assays for screening candidate or test compounds which bind to or modulate the activity of the membrane-bound form of an ADAM30 protein or polypeptide or biologically-active portion thereof. The test compounds of the disclosure can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. See, e.g., Lam, 1997. Anticancer Drug Design 12: 145.

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the disclosure.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (e.g., Houghten, 1992. Biotechniques 13: 412-421), or on beads (Lam, 1991. Nature 354: 82-84), on chips (Fodor, 1993. Nature 364: 555-556), bacteria (Ladner, U.S. Pat. No. 5,223,409), spores (Ladner, U.S. Pat. No. 5,233,409), plasmids (Cull, et al., 1992. Proc. Natl. Acad. Sci. USA 89: 1865-1869) or on phage (Scott and Smith, 1990. Science 249: 386-390; Devlin, 1990. Science 249: 404406; Cwirla, et al., 1990. Proc. Natl. Acad. Sci. U.S.A. 87: 6378-6382; Felici, 1991. J. Mol. Biol. 222: 301-310; Ladner, U.S. Pat. No. 5,233,409.).

In one embodiment, an assay is a cell-based assay in which a cell which expresses a membrane-bound form of ADAM30 protein, or a biologically-active portion thereof, on the cell surface is contacted with a test compound and the ability of the test compound to bind to an ADAM30 protein determined. The cell, for example, can of mammalian origin or a yeast cell. Determining the ability of the test compound to bind to the ADAM30 protein can be accomplished, for example, by coupling the test compound with a radioisotope or enzymatic label such that binding of the test compound to the ADAM30 protein or biologically-active portion thereof can be determined by detecting the labeled compound in a complex. For example, test compounds can be labeled with 125I, 35S, 14C, or 3H, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product. In one embodiment, the assay comprises contacting a cell which expresses a membrane-bound form of ADAM30 protein, or a biologically-active portion thereof, on the cell surface with a known compound which binds ADAM30 to form an assay mixture, contacting the assay mixture with a test compound, and determining the ability of the test compound to interact with an ADAM30 protein, wherein determining the ability of the test compound to interact with an ADAM30 protein comprises determining the ability of the test compound to preferentially bind to ADAM30 protein or a biologically-active portion thereof as compared to the known compound.

In another embodiment, an assay is a cell-based assay comprising contacting a cell expressing a membrane-bound form of ADAM30 protein, or a biologically-active portion thereof, on the cell surface with a test compound and determining the ability of the test compound to modulate (e.g., stimulate or inhibit) the activity of the ADAM30 protein or biologically-active portion thereof Determining the ability of the test compound to modulate the activity of ADAM30 or a biologically-active portion thereof can be accomplished, for example, by determining the ability of the ADAM30 protein to bind to or interact with an ADAM30 target molecule. As used herein, a "target molecule" is a molecule with which an ADAM30 protein binds or interacts in nature, for example, a molecule on the surface of a cell which expresses an ADAM30 interacting protein, a molecule on the surface of a second cell, a molecule in the extracellular milieu, a molecule associated with the internal surface of a cell membrane or a cytoplasmic molecule. An ADAM30 target molecule can be a non-ADAM30 molecule or an ADAM30 protein or polypeptide of the disclosure. In one embodiment, an ADAM30 target molecule is a component of a signal transduction pathway that facilitates transduction of an extracellular signal (e.g. a signal generated by binding of a compound to a membrane-bound ADAM30 molecule) through the cell membrane and into the cell. The target, for example, can be a second intercellular protein that has catalytic activity or a protein that facilitates the association of downstream signaling molecules with ADAM30.

Determining the ability of the ADAM30 protein to bind to or interact with an ADAM30 target molecule can be accomplished by one of the methods described above for determining direct binding. In one embodiment, determining the ability of the ADAM30 protein to bind to or interact with an ADAM30 target molecule can be accomplished by determining the activity of the target molecule. For example, the activity of the target molecule can be determined by detecting induction of a cellular second messenger of the target (i.e. intracellular $Ca^{2+}$, diacylglycerol, IP3, etc.), detecting catalytic/enzymatic activity of the target an appropriate substrate, detecting the induction of a reporter gene (comprising an ADAM30-responsive regulatory element operatively linked to a nucleic acid encoding a detectable marker, e.g., luciferase), or detecting a cellular response, for example, cell survival, cellular differentiation, or cell proliferation.

In yet another embodiment, an assay of the disclosure is a cell-free assay comprising contacting an ADAM30 protein or biologically-active portion thereof with a test compound and determining the ability of the test compound to bind to the ADAM30 protein or biologically-active portion thereof. Binding of the test compound to the ADAM30 protein can be determined either directly or indirectly as described above. In one such embodiment, the assay comprises contacting the ADAM30 protein or biologically-active portion thereof with a known compound which binds ADAM30 to form an assay mixture, contacting the assay mixture with a test compound, and determining the ability of the test compound to interact with an ADAM30 protein, wherein determining the ability of the test compound to interact with an ADAM30 protein comprises determining the ability of the test compound to preferentially bind to ADAM30 or biologically-active portion thereof as compared to the known compound.

In still another embodiment, an assay is a cell-free assay comprising contacting ADAM30 protein or biologically-active portion thereof with a test compound and determining the ability of the test compound to modulate (e.g. stimulate or inhibit) the activity of the ADAM30 protein or biologically-active portion thereof. Determining the ability of the test compound to modulate the activity of ADAM30 can be accomplished, for example, by determining the ability of the ADAM30 protein to bind to an ADAM30 target molecule by one of the methods described above for determining direct binding. In an alternative embodiment, determining the ability of the test compound to modulate the activity of ADAM30 protein can be accomplished by determining the ability of the ADAM30 protein further modulate an ADAM30 target molecule. For example, the catalytic/enzymatic activity of the target molecule on an appropriate substrate can be determined as described, supra.

In yet another embodiment, the cell-free assay comprises contacting the ADAM30 protein or biologically-active portion thereof with a known compound which binds ADAM30 protein to form an assay mixture, contacting the assay mixture with a test compound, and determining the ability of the test compound to interact with an ADAM30 protein, wherein determining the ability of the test compound to interact with an ADAM30 protein comprises determining the ability of the ADAM30 protein to preferentially bind to or modulate the activity of an ADAM30 target molecule.

The cell-free assays of the disclosure are amenable to use of both the soluble form or the membrane-bound form of ADAM30 protein. In the case of cell-free assays comprising the membrane-bound form of ADAM30 protein, it may be desirable to utilize a solubilizing agent such that the membrane-bound form of ADAM30 protein is maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)n, N-dodecyl-N,N-dimethyl-3-ammonio-1-propane sulfonate, 3-(3-cholamidopropyl)dimethylamminiol-1-propane sulfonate (CHAPS), or 3-(3-cholamidopropyl)dimethylamminiol-2-hydroxy-1-propane sulfonate (CHAPSO).

In more than one embodiment of the above assay methods of the disclosure, it may be desirable to immobilize either ADAM30 protein or its target molecule to facilitate separation of complexed from uncomplexed forms of one or both of the proteins, as well as to accommodate automation of the assay. Binding of a test compound to ADAM30 protein, or interaction of ADAM30 protein with a target molecule in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-ADAM30 fusion proteins or GST-target fusion proteins can be adsorbed onto glutathione sepharose beads (Sigma Chemical, St. Louis, Mo.) or glutathione derivatized microtiter plates, that are then combined with the test compound or the test compound and either the non-adsorbed target protein or ADAM30 protein, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described, supra. Alternatively, the complexes can be dissociated from the matrix, and the level of ADAM30 protein binding or activity determined using standard techniques.

Other techniques for immobilizing proteins on matrices can also be used in the screening assays of the disclosure. For example, either the ADAM30 protein or its target molecule can be immobilized utilizing conjugation of biotin and streptavidin. Biotinylated ADAM30 protein or target molecules can be prepared from biotin-NHS (N-hydroxy-succinimide) using techniques well-known within the art (e.g., biotinylation kit, Pierce Chemicals, Rockford, Ull.), and immobilized in the wells of streptavidin-coated 96 well plates (Pierce Chemical). Alternatively, antibodies reactive with ADAM30 protein or target molecules, but which do not interfere with binding of the ADAM30 protein to its target molecule, can be derivatized to the wells of the plate, and unbound target or ADAM30 protein trapped in the wells by antibody conjugation. Methods for detecting such complexes, in addition to those described above for the GST-immobilized complexes, include immunodetection of complexes using antibodies reactive with the ADAM30 protein or target molecule, as well as enzyme-linked assays that rely on detecting an enzymatic activity associated with the ADAM30 protein or target molecule.

In another embodiment, modulators of ADAM30 protein expression are identified in a method wherein a cell is contacted with a candidate compound and the expression of ADAM30 mRNA or protein in the cell is determined. The level of expression of ADAM30 mRNA or protein in the presence of the candidate compound is compared to the level of expression of ADAM30 mRNA or protein in the absence of the candidate compound. The candidate compound can then be identified as a modulator of ADAM30 mRNA or protein expression based upon this comparison. For example, when expression of ADAM30 mRNA or protein is greater (i.e., statistically significantly greater) in the presence of the candidate compound than in its absence, the candidate compound is identified as a stimulator of ADAM30 mRNA or protein expression. Alternatively, when expression of ADAM30 mRNA or protein is less (statistically significantly less) in the presence of the candidate compound than in its absence, the candidate compound is identified as an inhibitor of ADAM30 mRNA or protein expression. The level of ADAM30 mRNA or protein expression in the cells can be determined by methods described herein for detecting ADAM30 mRNA or protein.

In yet another aspect of the disclosure, the ADAM30 proteins can be used as "bait proteins" in a two-hybrid assay or three hybrid assay (see, e.g., U.S. Pat. No. 5,283,317; Zervos, et al., 1993. Cell 72: 223-232; Madura, et al., 1993. J. Biol. Chem. 268: 12046-12054; Bartel, et al., 1993. Biotechniques 14: 920-924; Iwabuchi, et al., 1993. Oncogene 8: 1693-1696; and Brent WO 94/10300), to identify other proteins that bind to or interact with ADAM30 ("ADAM30-binding proteins" or "ADAM30-bp") and modulate ADAM30 activity. Such ADAM30-binding proteins are also likely to be involved in the propagation of signals by the ADAM30 proteins as, for example, upstream or downstream elements of the ADAM30 pathway.

The two-hybrid system is based on the modular nature of most transcription factors, which consist of separable DNA-binding and activation domains. Briefly, the assay utilizes two different DNA constructs. In one construct, the gene that codes for ADAM30 is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming an ADAM30-dependent complex, the DNA-binding and activation domains of the transcription factor are brought into close proximity. This proximity allows transcription of a reporter gene (e.g., LacZ) that is operably linked to a transcriptional regulatory site responsive to the transcription factor. Expression of the reporter gene can be detected and cell colonies containing the functional transcription factor can be isolated and used to obtain the cloned gene that encodes the protein which interacts with ADAM30.

The disclosure further pertains to novel agents identified by the aforementioned screening assays and uses thereof for treatments as described herein.

Detection Assays

Portions or fragments of the cDNA sequences identified herein (and the corresponding complete gene sequences) can be used in numerous ways as polynucleotide reagents. By way of example, and not of limitation, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. Some of these applications are described in the subsections, below.

Chromosome Mapping

Once the sequence (or a portion of the sequence) of a gene has been isolated, this sequence can be used to map the location of the gene on a chromosome. This process is called chromosome mapping. Accordingly, portions or fragments of the ADAM30 sequences, SEQ ID NO: 1 or fragments or derivatives thereof, can be used to map the location of the ADAM30 genes, respectively, on a chromosome. The mapping of the ADAM30 sequences to chromosomes is an important first step in correlating these sequences with genes associated with disease.

Briefly, ADAM30 genes can be mapped to chromosomes by preparing PCR primers (preferably 15-25 bp in length) from the ADAM30 sequences. Computer analysis of the ADAM30, sequences can be used to rapidly select primers that do not span more than one exon in the genomic DNA, thus complicating the amplification process. These primers can then be used for PCR screening of somatic cell hybrids containing individual human chromosomes. Only those hybrids containing the human gene corresponding to the ADAM30 sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but in which human cells can, the one human chromosome that contains the gene encoding the needed enzyme will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. See, e.g., D'Eustachio, et al., 1983. Science 220: 919-924. Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the ADAM30 sequences to design oligonucleotide primers, sub-localization can be achieved with panels of fragments from specific chromosomes.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical like colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases, will suffice to get good results at a reasonable amount of time. For a review of this technique, see, Verma, et al., HUMAN CHROMOSOMES: A MANUAL OF BASIC TECHNIQUES (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. Such data are found, e.g., in McKusick, MENDELIAN INHERITANCE IN MAN, available on-line through Johns Hopkins University Welch Medical Library). The relationship between genes and disease, mapped to the same chromosomal region, can then be identified through linkage analysis (co-inheritance of physically adjacent genes), described in, e.g., Egeland, et al., 1987. Nature, 325: 783-787.

Moreover, differences in the DNA sequences between individuals affected and unaffected with a disease associated with the ADAM30 gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

Tissue Typing

The ADAM30 sequences of the disclosure can also be used to identify individuals from minute biological samples. In this technique, an individual's genomic DNA is digested with one or more restriction enzymes, and probed on a Southern blot to yield unique bands for identification. The sequences of the disclosure are useful as additional DNA markers for RFLP ("restriction fragment length polymorphisms," described in U.S. Pat. No. 5,272,057).

Furthermore, the sequences of the disclosure can be used to provide an alternative technique that determines the actual base-by-base DNA sequence of selected portions of an individual's genome. Thus, the ADAM30 sequences described herein can be used to prepare two PCR primers from the 5'- and 3'-termini of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the disclosure can be used to obtain such identification sequences from individuals and from tissue. The ADAM30 sequences of the disclosure uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Much of the allelic variation is due to single nucleotide polymorphisms (SNPs), which include restriction fragment length polymorphisms (RFLPs).

Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences can comfortably provide positive individual identification with a panel of perhaps 10 to 1,000 primers that each yield a noncoding amplified sequence of 100 bases. If predicted coding sequences, such as those in SEQ ID NO:1 are used, a more appropriate number of primers for positive individual identification would be 500-2,000.

Predictive Medicine

The disclosure also pertains to the field of predictive medicine in which diagnostic assays, prognostic assays, pharmacogenomics, and monitoring clinical trials are used for prognostic (predictive) purposes to thereby treat an individual prophylactically. Accordingly, one aspect of the disclosure relates to diagnostic assays for determining ADAM30 protein and/or nucleic acid expression as well as ADAM30 activity, in the context of a biological sample (e.g., blood, serum, cells, tissue) to thereby determine whether an individual is afflicted with a disease or disorder, or is at risk of developing a disorder, associated with aberrant ADAM30 expression or activity. The disorders include vascular disorders, disorders associated with chronic diseases, and various cancers. The disclosure also provides for prognostic (or predictive) assays for determining whether an individual is at risk of developing a disorder associated with ADAM30 protein, nucleic acid expression or activity. For example, mutations in an ADAM30 gene can be assayed in a biological sample. Such assays can be used for prognostic or predictive purpose to thereby prophylactically treat an individual prior to the onset of a disorder characterized by or associated with ADAM30 protein, nucleic acid expression, or biological activity.

Another aspect of the disclosure provides methods for determining ADAM30 protein, nucleic acid expression or activity in an individual to thereby select appropriate therapeutic or prophylactic agents for that individual (referred to herein as "pharmacogenomics"). Pharmacogenomics allows for the selection of agents (e.g., drugs) for therapeutic or prophylactic treatment of an individual based on the genotype of the individual (e.g., the genotype of the individual examined to determine the ability of the individual to respond to a particular agent.) Yet another aspect of the disclosure pertains to monitoring the influence of agents (e.g., drugs, compounds) on the expression or activity of ADAM30 in clinical trials.

These and other agents are described in further detail in the following sections.

Diagnostic Assays

An exemplary method for detecting the presence or absence of ADAM30 in a biological sample involves obtaining a biological sample from a test subject and contacting the biological sample with a compound or an agent capable of detecting ADAM30 protein or nucleic acid (e g., mRNA, genomic DNA) that encodes ADAM30 protein such that the presence of ADAM30 is detected in the biological sample. An agent for detecting ADAM30 mRNA or genomic DNA is a labeled nucleic acid probe capable of hybridizing to ADAM30 mRNA or genomic DNA. The nucleic acid probe can be, for example, a full-length ADAM30 nucleic acid, such as the nucleic acid of SEQ ID NO: 1, or a portion thereof, such as an oligonucleotide of at least 15, 30, 50, 100, 250 or 500 nucleotides in length and sufficient to specifically hybridize under stringent conditions to ADAM30 mRNA or genomic DNA. Other suitable probes for use in the diagnostic assays of the disclosure are described herein.

An agent for detecting ADAM30 protein is an antibody capable of binding to ADAM30 protein, preferably an antibody with a detectable label. Antibodies can be polyclonal, or more preferably, monoclonal. An intact antibody, or a fragment thereof (e.g., Fab or F(ab')2) can be used. The term "labeled", with regard to the probe or antibody, is intended to encompass direct labeling of the probe or antibody by coupling (ie., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the disclosure can be used to detect ADAM30 mRNA, protein, or genomic DNA in a biological sample in vitro as well as in vivo. For example, in vitro techniques for detection of ADAM30 mRNA include Northern hybridizations and in situ hybridizations. In vitro techniques for detection of ADAM30 protein include enzyme linked immunosorbent assays (ELISAs), Western blots, immunoprecipitations, and immunofluorescence. In vitro techniques for detection of ADAM30 genomic DNA include Southern hybridizations. Furthermore, in vivo techniques for detection of ADAM30 protein include introducing into a subject a labeled anti-ADAM30 antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a peripheral blood leukocyte sample isolated by conventional means from a subject.

In another embodiment, the methods further involve obtaining a control biological sample from a control subject, contacting the control sample with a compound or agent capable of detecting ADAM30 protein, mRNA, or genomic DNA, such that the presence of ADAM30 protein, mRNA or genomic DNA is detected in the biological sample, and comparing the presence of ADAM30 protein, mRNA or genomic DNA in the control sample with the presence of ADAM30 protein, mRNA or genomic DNA in the test sample.

The disclosure also encompasses kits for detecting the presence of ADAM30 in a biological sample. For example, the kit can comprise: a labeled compound or agent capable of detecting ADAM30 protein or mRNA in a biological sample; means for determining the amount of ADAM30 in the sample; and means for comparing the amount of ADAM30 in the sample with a standard. The compound or agent can be packaged in a suitable container. The kit can further comprise instructions for using the kit to detect ADAM30 protein or nucleic acid.

Prognostic Assays

The diagnostic methods described herein can furthermore be utilized to identify subjects having or at risk of developing a disease or disorder associated with aberrant ADAM30 expression or activity. For example, the assays described herein, such as the preceding diagnostic assays or the following assays, can be utilized to identify a subject having or at risk of developing a disorder associated with ADAM30 protein, nucleic acid expression or activity. Alternatively, the prognostic assays can be utilized to identify a subject having or at risk for developing a disease or disorder. Thus, the disclosure provides a method for identifying a disease or disorder associated with aberrant ADAM30 expression or activity in which a test sample is obtained from a subject and ADAM30 protein or nucleic acid (e.g., mRNA, genomic DNA) is detected, wherein the presence of ADAM30 protein or nucleic acid is diagnostic for a subject having or at risk of developing a disease or disorder associated with aberrant ADAM30 expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant ADAM30 expression or activity. For example, such methods can be used to determine whether a subject can be effectively treated with an agent for a disorder. Thus, the disclosure provides methods for determining whether a subject can be effectively treated with an agent for a disorder associated with aberrant ADAM30 expression or activity in which a test sample is obtained and ADAM30 protein or nucleic acid is detected (e.g., wherein the presence of ADAM30 protein or nucleic acid is diagnostic for a subject that can be administered the agent to treat a disorder associated with aberrant ADAM30 expression or activity).

The methods of the disclosure can also be used to detect genetic lesions in an ADAM30 gene, thereby determining if a subject with the lesioned gene is at risk for a disorder characterized by aberrant cell proliferation and/or differentiation. In various embodiments, the methods include detecting, in a sample of cells from the subject, the presence or absence of a genetic lesion characterized by at least one of an alteration affecting the integrity of a gene encoding an ADAM30-protein, or the misexpression of the ADAM30 gene. For example, such genetic lesions can be detected by ascertaining the existence of at least one of: (i) a deletion of one or more nucleotides from an ADAM30 gene; (ii) an addition of one or more nucleotides to an ADAM30 gene; (iii) a substitution of one or more nucleotides of an ADAM30 gene, (iv) a chromosomal rearrangement of an ADAM30 gene; (v) an alteration in the level of a messenger RNA transcript of an ADAM30 gene, (vi) aberrant modification of an ADAM30 gene, such as of the methylation pattern of the genomic DNA, (vii) the presence of a non-wild-type splicing pattern of a messenger RNA transcript of an ADAM30 gene, (viii) a non-wild-type level of an ADAM30 protein, (ix) allelic loss of an ADAM30 gene, and (x) inappropriate post-translational modification of an ADAM30 protein. As described herein, there are a large number of assay techniques known in the art which can be used for detecting lesions in an ADAM30 gene. A preferred biological sample is a peripheral blood leukocyte sample isolated by conventional means from a subject. However, any biological sample containing nucleated cells may be used, including, for example, buccal mucosal cells.

In certain embodiments, detection of the lesion involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran, et al., 1988. Science 241: 1077-1080; and Nakazawa, et al., 1994. Proc. Natl. Acad. Sci. USA 91: 360-364), the latter of which can be particularly useful for detecting point mutations in the ADAM30-gene (see, Abravaya, et al., 1995. Nucl. Acids Res. 23: 675-682). This method can include the steps of collecting a sample of cells from a patient, isolating nucleic acid (e.g., genomic, mRNA or both) from the cells of the sample, contacting the nucleic acid sample with one or more primers that specifically hybridize to an ADAM30 gene under conditions such that hybridization and amplification of the ADAM30 gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self-sustained sequence replication (see, Guatelli, et al., 1990. Proc. Natl. Acad. Sci. USA 87: 1874-1878), transcriptional amplification system (see, Kwoh, et al., 1989. Proc. Natl. Acad. Sci. USA 86:1173-1177); Qo Replicase (see, Lizardi, et al., 1988. BioTechnology 6: 1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in an ADAM30 gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, e.g., U.S. Pat. No. 5,493,531) can be used to score for the presence of specific mutations by development or loss of a ribozyme cleavage site.

In other embodiments, genetic mutations in ADAM30 can be identified by hybridizing a sample and control nucleic acids, e.g., DNA or RNA, to high-density arrays containing hundreds or thousands of oligonucleotides probes. See, e.g., Cronin, et al., 1996. Human Mutation 7: 244-255; Kozal, et al., 1996. Nat. Med. 2: 753-759. For example, genetic mutations in ADAM30 can be identified in two dimensional arrays containing light-generated DNA probes as described in Cronin, et al., supra. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the ADAM30 gene and detect mutations by comparing the sequence of the sample ADAM30 with the corresponding wild-type (control) sequence. Examples of sequencing reactions include those based on techniques developed by Maxim and Gilbert, 1977. Proc. Natl. Acad. Sci. USA 74: 560 or Sanger, 1977. Proc. Natl. Acad. Sci. USA 74: 5463. It is also contemplated that any of a variety of automated sequencing procedures can be utilized when performing the diagnostic assays (see, e.g., Naeve, et al., 1995. Biotechniques 19: 448), including sequencing by mass spectrometry (see, e.g., PCT International Publication No. WO 94/16101; Cohen, et al., 1996. Adv. Chromatography 36: 127-162; and Griffin, et al., 1993. Appl. Biochem. Biotechnol. 38: 147-159).

Other methods for detecting mutations in the ADAM30 gene include methods in which protection from cleavage agents is used to detect mismatched bases in RNA/RNA or RNA/DNA heteroduplexes. See, e.g., Myers, et al., 1985. Science 230: 1242. In general, the art technique of "mismatch cleavage" starts by providing heteroduplexes of formed by hybridizing (labeled) RNA or DNA containing the wild-type ADAM30 sequence with potentially mutant RNA or DNA obtained from a tissue sample. The double-stranded duplexes are treated with an agent that cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, e.g., Cotton, et al., 1988. Proc. Natl. Acad. Sci. USA 85: 4397; Saleeba, et al., 1992. Methods Enzymol. 217: 286-295. In an embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in ADAM30 cDNAs obtained from samples of cells. For example, the mutY enzyme of *E. coli* cleaves A at G/A mismatches and the thymidine DNA glycosylase from HeLa cells cleaves T at G/T mismatches. See, e.g., Hsu, et al., 1994. Carcinogenesis 15: 1657-1662. According to an exemplary embodiment, a probe based on an ADAM30 sequence, e.g., a wild-type ADAM30 sequence, is hybridized to a cDNA or other DNA product from a test cell(s). The duplex is treated with a DNA mismatch repair enzyme, and the cleavage products, if any, can be detected from electrophoresis protocols or the like. See, e.g., U.S. Pat. No. 5,459,039.

In other embodiments, alterations in electrophoretic mobility will be used to identify mutations in ADAM30 genes. For example, single strand conformation polymorphism (SSCP) may be used to detect differences in electrophoretic mobility between mutant and wild type nucleic acids. See, e.g., Orita, et al., 1989. Proc. Natl. Acad. Sci. USA: 86: 2766; Cotton, 1993. Mutat. Res. 285: 125-144; Hayashi, 1992. Genet. Anal. Tech. Appl. 9: 73-79. Single-stranded DNA fragments of sample and control ADAM30 nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In one embodiment, the subject method utilizes heteroduplex analysis to separate double stranded heteroduplex molecules on the basis of changes in electrophoretic mobility. See, e.g., Keen, et al., 1991. Trends Genet. 7: 5.

In yet another embodiment, the movement of mutant or wild-type fragments in polyacrylamide gels containing a gradient of denaturant is assayed using denaturing gradient gel electrophoresis (DGGE). See, e.g., Myers, et al., 1985. Nature 313: 495. When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control and sample DNA. See, e.g., Rosenbaum and Reissner, 1987. Biophys. Chem. 265: 12753.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. See, e.g., Saiki, et al., 1986. Nature 324: 163; Saiki, et al., 1989. Proc. Natl. Acad. Sci. USA 86: 6230. Such allele specific oligonucleotides are hybridized to PCR amplified target DNA or a number of different mutations when the oligonucleotides are attached to the hybridizing membrane and hybridized with labeled target DNA.

Alternatively, allele specific amplification technology that depends on selective PCR amplification may be used in conjunction with the instant disclosure. Oligonucleotides used as primers for specific amplification may carry the mutation of interest in the center of the molecule (so that amplification depends on differential hybridization; see, e.g., Gibbs, et al., 1989. Nucl. Acids Res. 17: 2437-2448) or at the extreme 3'-terminus of one primer where, under appropriate conditions, mismatch can prevent, or reduce polymerase extension (see, e.g., Prossner, 1993. Tibtech. 11: 238). In addition it may be desirable to introduce a novel restriction site in the region of the mutation to create cleavage-based detection. See, e.g., Gasparini, et al., 1992. Mol. Cell Probes 6: 1. It is anticipated that in certain embodiments amplification may also be performed using Taq ligase for amplification. See, e.g., Barany, 1991. Proc. Natl. Acad. Sci. USA 88: 189. In such cases, ligation will occur only if there is a perfect match at the 3'-terminus of the 5' sequence, making it possible to detect the presence of a known mutation at a specific site by looking for the presence or absence of amplification.

The methods described herein may be performed, for example, by utilizing pre-packaged diagnostic kits comprising at least one probe nucleic acid or antibody reagent described herein, which may be conveniently used, e.g., in clinical settings to diagnose patients exhibiting symptoms or family history of a disease or illness involving an ADAM30 gene.

Furthermore, any cell type or tissue, preferably peripheral blood leukocytes, in which ADAM30 is expressed may be utilized in the prognostic assays described herein. However, any biological sample containing nucleated cells may be used, including, for example, buccal mucosal cells.

Pharmacogenomics

Agents, or modulators that have a stimulatory or inhibitory effect on ADAM30 activity (e.g., ADAM30 gene expression), as identified by a screening assay described herein can be administered to individuals to treat (prophylactically or therapeutically) disorders (The disorders include vascular disorders, cancer-associated, and various cancers.) In conjunction with such treatment, the pharmacogenomics (i.e., the study of the relationship between an individual's genotype and that individual's response to a foreign compound or drug) of the individual may be considered. Differences in metabolism of therapeutics can lead to severe toxicity or therapeutic failure by altering the relation between dose and blood concentration of the pharmacologically active drug. Thus, the pharmnacogenomics of the individual permits the selection of effective agents (e.g., drugs) for prophylactic or therapeutic treatments based on a consideration of the individual's genotype. Such pharmnacogenomics can further be used to determine appropriate dosages and therapeutic regimens. Accordingly, the activity of ADAM30 protein, expression of ADAM30 nucleic acid, or mutation content of ADAM30 genes in an individual can be determined to thereby select appropriate agent(s) for therapeutic or prophylactic treatment of the individual.

Pharmacogenomics deals with clinically significant hereditary variations in the response to drugs due to altered drug disposition and abnormal action in affected persons. See e.g., Eichelbaum, 1996. Clin. Exp. Pharmacol. Physiol., 23: 983-985; Linder, 1997. Clin. Chem., 43: 254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare defects or as polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C 19 quite frequently experience exaggerated drug response and side effects when they receive standard doses. If a metabolite is the active therapeutic moiety, PM show no therapeutic response, as demonstrated for the analgesic effect of codeine mediated by its CYP2D6-formed metabolite morphine. At the other extreme are the so called ultra-rapid metabolizers who do not respond to standard doses. Recently, the molecular basis of ultra-rapid metabolism has been identified to be due to CYP2D6 gene amplification.

Thus, the activity of ADAM30 protein, expression of ADAM30 nucleic acid, or mutation content of ADAM30 genes in an individual can be determined to thereby select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with an ADAM30 modulator, such as a modulator identified by one of the exemplary screening assays described herein.

Monitoring of Effects During Clinical Trials

Monitoring the influence of agents (e.g., drugs, compounds) on the expression or activity of ADAM30 (e.g., the ability to modulate aberrant cell proliferation and/or differentiation) can be applied not only in basic drug screening, but also in clinical trials. For example, the effectiveness of an agent determined by a screening assay as described herein to increase ADAM30 gene expression, protein levels, or upregulate ADAM30 activity, can be monitored in clinical trials of subjects exhibiting decreased ADAM30 gene expression, protein levels, or downregulated ADAM30 activity. Alternatively, the effectiveness of an agent determined by a screening assay to decrease ADAM30 gene expression, protein levels, or downregulate ADAM30 activity, can be monitored in clinical trials of subjects exhibiting increased ADAM30 gene expression, protein levels, or upregulated ADAM30 activity. In such clinical trials, the expression or activity of ADAM30 and, preferably, other genes that have been implicated in, for example, a cellular proliferation or immune disorder can be used as a "read out" or markers of the immune responsiveness of a particular cell.

By way of example, and not of limitation, genes, including ADAM30, that are modulated in cells by treatment with an agent (e.g., compound, drug or small molecule) that modulates ADAM30 activity (e.g., identified in a screening assay as described herein) can be identified. Thus, to study the effect of agents on cellular proliferation disorders, for example, in a clinical trial, cells can be isolated and RNA prepared and analyzed for the levels of expression of ADAM30 and other genes implicated in the disorder. The levels of gene expression (i.e., a gene expression pattern) can be quantified by Northern blot analysis or RT-PCR, as described herein, or alternatively by measuring the amount of protein produced, by one of the methods as described herein, or by measuring the levels of activity of ADAM30 or other genes. In this manner, the gene expression pattern can serve as a marker, indicative of the physiological response of the cells to the agent. Accordingly, this response state may be determined before, and at various points during, treatment of the individual with the agent.

In one embodiment, the disclosure provides a method for monitoring the effectiveness of treatment of a subject with an agent (e.g., an agonist, antagonist, protein, peptide, peptidomimetic, nucleic acid, small molecule, or other drug candidate identified by the screening assays described herein) comprising the steps of (i) obtaining a pre-administration sample from a subject prior to administration of the agent; (ii) detecting the level of expression of an ADAM30 protein, mRNA, or genomic DNA in the preadministration sample; (iii) obtaining one or more post-administration samples from the subject; (iv) detecting the level of expression or activity of the ADAM30 protein, mRNA, or genomic DNA in the post-administration samples; (v) comparing the level of expression or activity of the ADAM30 protein, mRNA, or genomic DNA in the pre-administration sample with the ADAM30 protein, mRNA, or genomic DNA in the post administration sample or samples; and (vi) altering the administration of the agent to the subject accordingly. For example, increased administration of the agent may be desirable to increase the expression or activity of ADAM30 to higher levels than detected, i.e., to increase the effectiveness of the agent. Alternatively, decreased administration of the agent may be desirable to decrease expression or activity of ADAM30 to lower levels than detected, i.e., to decrease the effectiveness of the agent.

Methods of Treatment

The disclosure provides for both prophylactic and therapeutic methods of treating a subject at risk of (or susceptible to) a disorder or having a disorder associated with aberrant ADAM30 expression or activity. The disorders include vascular disorders and cancers, and other diseases, disorders and conditions of the like.

These methods of treatment will be discussed more fully below.

Disease and Disorders

Diseases and disorders that are characterized by increased (relative to a subject not suffering from the disease or disorder) levels or biological activity may be treated with Therapeutics that antagonize (i e., reduce or inhibit) activity. Therapeutics that antagonize activity may be administered in a therapeutic or prophylactic manner. Therapeutics that may be utilized include, but are not limited to: (i) an aforementioned peptide, or analogs, derivatives, fragments or homologs thereof; (ii) antibodies to an aforementioned peptide; (iii) nucleic acids encoding an aforementioned peptide; (iv) administration of antisense nucleic acid and nucleic acids that are "dysfunctional" (i.e., due to a heterologous insertion within the coding sequences of coding sequences to an aforementioned peptide) that are utilized to "knockout" endogenous function of an aforementioned peptide by homologous recombination (see, e.g., Capecchi, 1989. Science 244: 1288-1292); or (v) modulators (i.e., inhibitors, agonists and antagonists, including additional peptide mimetic of the disclosure or antibodies specific to a peptide of the disclosure) that alter the interaction between an aforementioned peptide and its binding partner.

Diseases and disorders that are characterized by decreased (relative to a subject not suffering from the disease or disorder) levels or biological activity may be treated with Therapeutics that increase (ie., are agonists to) activity. Therapeutics that upregulate activity may be administered in a therapeutic or prophylactic manner. Therapeutics that may be utilized include, but are not limited to, an aforementioned peptide, or analogs, derivatives, fragments or homologs thereof; or an agonist that increases bioavailability.

Increased or decreased levels can be readily detected by quantifying peptide and/or RNA, by obtaining a patient tissue sample (e.g., from biopsy tissue) and assaying it in vitro for RNA or peptide levels, structure and/or activity of the expressed peptides (or mRNAs of an aforementioned peptide). Methods that are well-known within the art include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

Prophylactic Methods

In one aspect, the disclosure provides a method for preventing, in a subject, a disease or condition associated with an aberrant ADAM30 expression or activity, by administering to the subject an agent that modulates ADAM30 expression or at least one ADAM30 activity. Subjects at risk for a disease that is caused or contributed to by aberrant ADAM30 expression or activity can be identified by, for example, any or a combination of diagnostic or prognostic assays as described herein. Administration of a prophylactic agent can occur prior to the manifestation of symptoms characteristic of the ADAM30 aberrancy, such that a disease or disorder is prevented or, alternatively, delayed in its progression. Depending upon the type of ADAM30 aberrancy, for example, an ADAM30 agonist or ADAM30 antagonist agent can be used for treating the subject. The appropriate agent can be determined based on screening assays described herein. The prophylactic methods of the disclosure are further discussed in the following subsections.

Therapeutic Methods

Another aspect of the disclosure pertains to methods of modulating ADAM30 expression or activity for therapeutic purposes. The modulatory method of the disclosure involves contacting a cell with an agent that modulates one or more of the activities of ADAM30 protein activity associated with the cell. An agent that modulates ADAM30 protein activity can be an agent as described herein, such as a nucleic acid or a protein, a naturally-occurring cognate ligand of an ADAM30 protein, a peptide, an ADAM30 peptidomimetic, or other small molecule. In one embodiment, the agent stimulates one or more ADAM30 protein activity. Examples of such stimulatory agents include active ADAM30 protein and a nucleic acid molecule encoding ADAM30 that has been introduced into the cell. In another embodiment, the agent inhibits one or more ADAM30 protein activity. Examples of such inhibitory agents include antisense ADAM30 nucleic acid molecules and anti-ADAM30 antibodies. These modulatory methods can be performed in vitro (e.g., by culturing the cell with the agent) or, alternatively, in vivo (e.g., by administering the agent to a subject). As such, the disclosure provides methods of treating an individual afflicted with a disease or disorder characterized by aberrant expression or activity of an ADAM30 protein or nucleic acid molecule. In one embodiment, the method involves administering an agent (e.g., an agent identified by a screening assay described herein), or combination of agents that modulates (e.g., up-regulates or down-regulates) ADAM30 expression or activity. In another embodiment, the method involves administering an ADAM30 protein or nucleic acid molecule as therapy to compensate for reduced or aberrant ADAM30 expression or activity.

Stimulation of ADAM30 activity is desirable in situations in which ADAM30 is abnormally downregulated and/or in which increased ADAM30 activity is likely to have a beneficial effect. One example of such a situation is where a subject has a disorder characterized by aberrant cell proliferation and/or differentiation (e.g., cancer).

Determination of the Biological Effect of the Therapeutic

In various embodiments of the disclosure, suitable in vitro or in vivo assays are performed to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon the cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of the Compositions of the Disclosure

The ADAM30 nucleic acids and proteins of the disclosure are useful in potential prophylactic and therapeutic applications implicated in a variety of disorders including, but not limited to: vascular disorders and various cancers.

As an example, a cDNA encoding the ADAM30 protein of the disclosure may be useful in gene therapy, and the protein may be useful when administered to a subject in need thereof. By way of non-limiting example, the compositions of the disclosure will have efficacy for treatment of vascular disorders and various cancers.

Both the novel nucleic acid encoding the ADAM30 protein, and the ADAM30 protein of the disclosure, or fragments thereof, may also be useful in diagnostic applications, wherein the presence or amount of the nucleic acid or the protein are to be assessed. A further use could be as an anti-bacterial molecule (i.e., some peptides have been found to possess anti-bacterial properties). These materials are further useful in the generation of antibodies, which immunospecifically-bind to the novel substances of the disclosure for use in therapeutic or diagnostic methods.

General Screening and Diagnostic Methods

Several of the herein disclosed methods relate to comparing the levels of expression of angiopoietin related protein (ARP) nucleic acids or polypeptides in a test and reference cell populations. The sequence information disclosed herein, coupled with nucleic acid detection methods known in the art, allow for detection and comparison of the ARP transcripts.

In its various aspects and embodiments, the disclosure includes providing a test cell population which includes at least one cell that is capable of expressing ARP. By "capable of expressing" is meant that the gene is present in an intact form in the cell and is expressed under particular conditions. Using sequence information provided by the database entries for the ARP sequences, ARP sequences can be detected (if present) and measured using techniques well known to one of ordinary skill in the art. For example, sequences within the sequence database entries corresponding to ARP, or within the sequences disclosed herein, can be used to construct probes for detecting ARP RNA sequences in, e.g., northern blot hybridization analyses or methods which specifically, and, preferably, quantitatively amplify specific nucleic acid sequences. As another example, the sequences can be used to construct primers for specifically amplifying the ARP sequences in, e.g., amplification-based detection methods such as reverse-transcription based polymerase chain reaction. When alterations in gene expression are associated with gene amplification or deletion, sequence comparisons in test and reference populations can be made by comparing relative amounts of the examined DNA sequences in the test and reference cell populations.

For ARP sequences whose polypeptide product is known, expression can be also measured at the protein level, i.e., by measuring the levels of polypeptides encoded by the gene products described herein. Such methods are well known in the art and include, e.g., immunoassays based on antibodies to proteins encoded by the genes.

Expression level of the ARP sequences in the test cell population is then compared to expression levels of the ARP in one or more cells from a reference cell population. Expression of sequences in test and control populations of cells can be compared using any art-recognized method for comparing expression of nucleic acid sequences. For example, expression can be compared using GENECALL-ING® methods as described in U.S. Pat. No. 5,871,697 and in Shimkets et al., Nat. Biotechnol. 17:798-803.

In various embodiments, the expression of ARP are measured. If desired, expression of these sequences can be measured along with other sequences whose expression is known to be altered according to one of the herein described parameters or conditions.

The reference cell population includes one or more cells capable of expressing the measured ARP sequences and for which the compared parameter is known, e.g., exposed to a test agent, disease status or ADAM30 expression status. By "disease status" is meant is known whether the reference cell has the disease state being screened (e.g., vascular disorders and various cancers). By "ADAM30 expression status" is meant that is known whether the reference cell has had contact with a ADAM30 ligand. Whether or not comparison of the gene expression profile in the test cell population to the reference cell population reveals the presence, or degree, of the measured parameter depends on the composition of the reference cell population. For example, if the reference cell population is composed of cells that have not been treated with a known ADAM30 ligand, a similar gene expression level in the test cell population and a reference cell population indicates the test agent is not a ADAM30 ligand. Conversely, if the reference cell population is made up of cells that have been treated with a known ADAM30 ligand, a similar gene expression profile between the test cell population and the reference cell population indicates the test agent is a ADAM30 ligand.

In various embodiments, a ARP sequence in a test cell population is considered comparable in expression level to the expression level of the ARP sequence if its expression level varies within a factor of 2.0, 1.5, or 1.0 fold to the level of the ARP transcript in the reference cell population. In various embodiments, a ARP sequence in a test cell population can be considered altered in levels of expression if its expression level varies from the reference cell population by more than 1.0, 1.5, 2.0 or more fold from the expression level of the corresponding ARP sequence in the reference cell population.

If desired, comparison of differentially expressed sequences between a test cell population and a reference cell population can be done with respect to a control nucleic acid whose expression is independent of the parameter or condition being measured. Expression levels of the control nucleic acid in the test and reference nucleic acid can be used to normalize signal levels in the compared populations. Suitable control nucleic acids can readily be determined by one of ordinary skill in the art.

In some embodiments, the test cell population is compared to multiple reference cell populations. Each of the multiple reference populations may differ in the known parameter. For example, a test cell population may be compared to a first reference cell population known to have been exposed to a ADAM30 ligand, as well as a second reference population known have not been exposed to a ADAM30 ligand.

The test cell population that is exposed to, i.e., contacted with, the test ligand can be any number of cells, i.e., one or more cells, and can be provided in vitro, in vivo, or ex vivo.

In other embodiments, the test cell population can be divided into two or more subpopulations. The subpopulations can be created by dividing the first population of cells to create as identical a subpopulation as possible. This will be suitable, in, for example, in vitro or ex vivo screening methods. In some embodiments, various sub populations can be exposed to a control agent, and/or a test agent, multiple test agents, or, e.g., varying dosages of one or multiple test agents administered together, or in various combinations.

Preferably, cells in the reference cell population are derived from a tissue type as similar as possible to test cell, e.g., adipose tissue or liver tissue. In some embodiments, the control cell is derived from the same subject as the test cell, e.g., from a region proximal to the region of origin of the test cell. In other embodiments, the reference cell population is derived from a plurality of cells For example, the reference cell population can be a database of expression patterns from previously tested cells for which one of the herein-described parameters or conditions (e.g., ADAM30 status, screening, diagnostic, or therapeutic claims) is known.

The subject is preferably a mammal. The mammal can be, e.g., a human, non-human primate, mouse, rat, dog, cat, horse, or cow.

Screening for Therapeutic Agents

In one aspect, the disclosure provides a method screening for therapeutic agents. By "therapeutic agent" is meant an agent that promotes a therapeutic effects such as a chemotherapeutic compound.

Expression of the nucleic acid sequences in the test cell population is then compared to the expression of the nucleic acid sequences in a reference cell population, which is a cell population that has not been exposed to the test agent, or, in some embodiments, a cell population exposed the test agent. Comparison can be performed on test and reference samples measured concurrently or at temporally distinct times. An example of the latter is the use of compiled expression information, e.g., a sequence database, which assembles information about expression levels of known sequences following administration of various agents. For example, alteration of expression levels following administration of test agent can be compared to the expression changes observed in the nucleic acid sequences following administration of a control agent, parathyroid hormone An alteration in expression of the nucleic acid sequence in the test cell population compared to the expression of the nucleic acid sequence in the reference cell population that has not been exposed to the test agent indicates the test agent is an therapeutic agent.

The disclosure also includes the therapeutic agent identified according to this screening method, and a pharmaceutical composition which includes the therapeutic agent.

In its various aspects and embodiments, the disclosure includes administering to a subject or contacting a cell with a compound that decrease ARP expression or activity. The compound can be, e.g., (i) an antibody or biologically active fragment thereof that specifically binds ARP; (ii) an anti-sense ARP nucleic acid; (iii) a ribozyme that specifically targets ARP (iv) a nucleic acid that decrease the expression of a nucleic acid that encodes an ARP polypeptide, and derivatives, fragments, analogs and homologs thereof and (v) small molecule ARP antagonists.

The antibody can be for example, monoclonal, polyclonal, humanized, radiolabled, or bispecific. The nucleic acid can be either endogenous or exogenous.

As used herein, the term "nucleic acid" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded. The nucleic acid can be either endogenous or exogenous. Preferably, the nucleic acid is a DNA.

The compound can be administered to the subject either directly (i.e., the subject is directly exposed to the nucleic acid or nucleic acid-containing vector) or indirectly (i.e., cells are first transformed with the nucleic acid in vitro, then transplanted into the subject). For example, in one embodiment mammalian cells are isolated from a subject and the ARP anti-sense nucleic acid is introduced into the isolated cells in vitro. The cells are reintroduced into a suitable mammalian subject. Preferably, the cell is introduced into an autologous subject. The routes of administration of the compound can include e.g., parenteral, intravenous, intradermal, subcutaneous, oral (e.g., inhalation), transdermal (topical), transmucosal, and rectal administration. In one embodiment the compound is administered intravenous.

The subject can be, e.g., a human, a rodent such as a mouse or rat, or a dog or cat.

```
SEQUENCE LISTING
<110> University of South Carolina
<120> TARGETING TREATMENT FOR ADAM30 IN PATHOLOGICAL CELLS
<130> 2033101.0000158
<140> Unknown
<141> 2021 Aug. 12
<150> U.S. Provisional Application No. 63/090,382
<151> Oct. 12, 2020
<160> 1
<170> PatentIn
<210> 1
<211> 790
<212> PRT
<213> Homo sapiens
<221> CDS
<222> 1 . . . 790
<400> 1
            10          20          30          40          50
    MRSVQIFLSQ CRLLLLLVPT MLLKSLGEDV IFHPEGEFDS YEVTIPEKLS 60          70          80          90         100
    FRGEVQGVVS PVSYLLQLKG KKHVLHLWPK RLLLPRHLRV FSFTEHGELL
```

```
              110        120        130        140        150
       EDHPYIPKDC NYMGSVKESL DSKATISTCM GGLRGVFNID AKHYQIEPLK 160        170        180        190        200
       ASPSFEHVVY LLKKEQFGNQ VCGLSDDEIE WQMAPYENKA RLRDFPGSYK 210        220        230        240        250
       HPKYLELILL FDQSRYRFVN NNLSQVIHDA ILLTGIMDTY FQDVRMRIHL 260        270        280        290        300
       KALEVWTDFN KIRVGYPELA EVLGRFVIYK KSVLNARLSS DWAHLYLQRK 310        320        330        340        350
       YNDALAWSFG KVCSLEYAGS VSTLLDTNIL APATWSAHEL GHAVGMSHDE 360        370        380        390        400
       QYCQCRGRLN CIMGSGRTGF SNCSYISFFK HISSGATCLN NIPGLGYVLK 410        420        430        440        450
       RCGNKIVEDN EECDCGSTEE CQKDRCCQSN CKLQPGANCS IGLCCHDCRF 460        470        480        490        500
       RPSGYVCRQE GNECDLAEYC DGNSSSCPND VYKQDGTPCK YEGRCFRKGC 510        520        530        540        550
       RSRYMQCQSI FGPDAMEAPS ECYDAVNLIG DQFGNCEITG IRNFKKCESA 560        570        580        590        600
       NSICGRLQCI NVETIPDLPE HTTIISTHLQ AENLMCWGTG YHLSMKPMGI 610        620        630        640        650
       PDLGMINDGT SCGEGRVCFK KNCVNSSVLQ FDCLPEKCNT RGVCNNRKNC 660        670        680        690        700
       HCMYGWAPPF CEEVGYGGSI DSGPPGLLRG AIPSSIWVVS IIMFRLILLI 710        720        730        740        750
       LSVVFVFFRQ VIGNHLKPKQ EKMPLSKAKT EQEESKTKTV QEESKTKTGQ 760        770        780        790
       EESEAKTGQE ESKAKTGQEE SKANIESERP KAKSVKKQKK
```

The figures herein are for illustrative purposes only and are not necessarily drawn to scale.

Various modifications and variations of the described methods, pharmaceutical compositions, and kits of the disclosure will be apparent to those skilled in the art without departing from the scope and spirit of the disclosure. Although the disclosure has been described in connection with specific embodiments, it will be understood that it is capable of further modifications and that the disclosure as claimed should not be unduly limited to such specific embodiments. Indeed, various modifications of the described modes for carrying out the disclosure that are obvious to those skilled in the art are intended to be within the scope of the disclosure. This application is intended to cover any variations, uses, or adaptations of the disclosure following, in general, the principles of the disclosure and including such departures from the present disclosure come within known customary practice within the art to which the disclosure pertains and may be applied to the essential features herein before set forth.

---

SEQUENCE LISTING

```
<160> NUMBER OF SEQ ID NOS: 1

<210> SEQ ID NO 1
<211> LENGTH: 790
<212> TYPE: PRT
<213> ORGANISM: Homo sapiens

<400> SEQUENCE: 1

Met Arg Ser Val Gln Ile Phe Leu Ser Gln Cys Arg Leu Leu Leu
1               5                   10                  15

Leu Val Pro Thr Met Leu Leu Lys Ser Leu Gly Glu Asp Val Ile Phe
                20                  25                  30

His Pro Glu Gly Glu Phe Asp Ser Tyr Glu Val Thr Ile Pro Glu Lys
            35                  40                  45

Leu Ser Phe Arg Gly Glu Val Gln Gly Val Val Ser Pro Val Ser Tyr
```

```
            50                  55                  60
Leu Leu Gln Leu Lys Gly Lys Lys His Val Leu His Leu Trp Pro Lys
 65                  70                  75                  80

Arg Leu Leu Leu Pro Arg His Leu Arg Val Phe Ser Phe Thr Glu His
                 85                  90                  95

Gly Glu Leu Leu Glu Asp His Pro Tyr Ile Pro Lys Asp Cys Asn Tyr
                100                 105                 110

Met Gly Ser Val Lys Glu Ser Leu Asp Ser Lys Ala Thr Ile Ser Thr
                115                 120                 125

Cys Met Gly Gly Leu Arg Gly Val Phe Asn Ile Asp Ala Lys His Tyr
            130                 135                 140

Gln Ile Glu Pro Leu Lys Ala Ser Pro Ser Phe Glu His Val Val Tyr
145                 150                 155                 160

Leu Leu Lys Lys Glu Gln Phe Gly Asn Gln Val Cys Gly Leu Ser Asp
                165                 170                 175

Asp Glu Ile Glu Trp Gln Met Ala Pro Tyr Glu Asn Lys Ala Arg Leu
                180                 185                 190

Arg Asp Phe Pro Gly Ser Tyr Lys His Pro Lys Tyr Leu Glu Leu Ile
            195                 200                 205

Leu Leu Phe Asp Gln Ser Arg Tyr Arg Phe Val Asn Asn Asn Leu Ser
        210                 215                 220

Gln Val Ile His Asp Ala Ile Leu Leu Thr Gly Ile Met Asp Thr Tyr
225                 230                 235                 240

Phe Gln Asp Val Arg Met Arg Ile His Leu Lys Ala Leu Glu Val Trp
                245                 250                 255

Thr Asp Phe Asn Lys Ile Arg Val Gly Tyr Pro Glu Leu Ala Glu Val
                260                 265                 270

Leu Gly Arg Phe Val Ile Tyr Lys Lys Ser Val Leu Asn Ala Arg Leu
            275                 280                 285

Ser Ser Asp Trp Ala His Leu Tyr Leu Gln Arg Lys Tyr Asn Asp Ala
        290                 295                 300

Leu Ala Trp Ser Phe Gly Lys Val Cys Ser Leu Glu Tyr Ala Gly Ser
305                 310                 315                 320

Val Ser Thr Leu Leu Asp Thr Asn Ile Leu Ala Pro Ala Thr Trp Ser
                325                 330                 335

Ala His Glu Leu Gly His Ala Val Gly Met Ser His Asp Glu Gln Tyr
            340                 345                 350

Cys Gln Cys Arg Gly Arg Leu Asn Cys Ile Met Gly Ser Gly Arg Thr
        355                 360                 365

Gly Phe Ser Asn Cys Ser Tyr Ile Ser Phe Phe Lys His Ile Ser Ser
    370                 375                 380

Gly Ala Thr Cys Leu Asn Asn Ile Pro Gly Leu Gly Tyr Val Leu Lys
385                 390                 395                 400

Arg Cys Gly Asn Lys Ile Val Glu Asp Asn Glu Glu Cys Asp Cys Gly
                405                 410                 415

Ser Thr Glu Glu Cys Gln Lys Asp Arg Cys Cys Gln Ser Asn Cys Lys
            420                 425                 430

Leu Gln Pro Gly Ala Asn Cys Ser Ile Gly Leu Cys Cys His Asp Cys
        435                 440                 445

Arg Phe Arg Pro Ser Gly Tyr Val Cys Arg Gln Glu Gly Asn Glu Cys
    450                 455                 460

Asp Leu Ala Glu Tyr Cys Asp Gly Asn Ser Ser Ser Cys Pro Asn Asp
465                 470                 475                 480
```

-continued

```
Val Tyr Lys Gln Asp Gly Thr Pro Cys Lys Tyr Glu Gly Arg Cys Phe
                485                 490                 495

Arg Lys Gly Cys Arg Ser Arg Tyr Met Gln Cys Gln Ser Ile Phe Gly
            500                 505                 510

Pro Asp Ala Met Glu Ala Pro Ser Glu Cys Tyr Asp Ala Val Asn Leu
            515                 520                 525

Ile Gly Asp Gln Phe Gly Asn Cys Glu Ile Thr Gly Ile Arg Asn Phe
            530                 535                 540

Lys Lys Cys Glu Ser Ala Asn Ser Ile Cys Gly Arg Leu Gln Cys Ile
545                 550                 555                 560

Asn Val Glu Thr Ile Pro Asp Leu Pro Glu His Thr Thr Ile Ile Ser
                565                 570                 575

Thr His Leu Gln Ala Glu Asn Leu Met Cys Trp Gly Thr Gly Tyr His
                580                 585                 590

Leu Ser Met Lys Pro Met Gly Ile Pro Asp Leu Gly Met Ile Asn Asp
                595                 600                 605

Gly Thr Ser Cys Gly Glu Gly Arg Val Cys Phe Lys Lys Asn Cys Val
                610                 615                 620

Asn Ser Ser Val Leu Gln Phe Asp Cys Leu Pro Glu Lys Cys Asn Thr
625                 630                 635                 640

Arg Gly Val Cys Asn Asn Arg Lys Asn Cys His Cys Met Tyr Gly Trp
                645                 650                 655

Ala Pro Pro Phe Cys Glu Glu Val Gly Tyr Gly Gly Ser Ile Asp Ser
                660                 665                 670

Gly Pro Pro Gly Leu Leu Arg Gly Ala Ile Pro Ser Ser Ile Trp Val
            675                 680                 685

Val Ser Ile Ile Met Phe Arg Leu Ile Leu Leu Ile Leu Ser Val Val
            690                 695                 700

Phe Val Phe Phe Arg Gln Val Ile Gly Asn His Leu Lys Pro Lys Gln
705                 710                 715                 720

Glu Lys Met Pro Leu Ser Lys Ala Lys Thr Glu Gln Glu Glu Ser Lys
                725                 730                 735

Thr Lys Thr Val Gln Glu Glu Ser Lys Thr Lys Thr Gly Gln Glu Glu
            740                 745                 750

Ser Glu Ala Lys Thr Gly Gln Glu Glu Ser Lys Ala Lys Thr Gly Gln
            755                 760                 765

Glu Glu Ser Lys Ala Asn Ile Glu Ser Glu Arg Pro Lys Ala Lys Ser
        770                 775                 780

Val Lys Lys Gln Lys Lys
785                 790
```

What is claimed is:

1. Methods for detecting congenital vascular malformations comprising:
   obtaining at least one body fluid sample from a subject;
   introducing at least one human or humanized antibody having at least two binding specificities for at least two different antigens to the at least one body fluid sample wherein the at least one human or humanized antibody compound is configured to bind to at least one domain of at least one biomarker comprising an ADAM30 protein or polypeptide thereof present in the at least one body fluid sample;
   wherein binding of the at least one human or humanized antibody to the at least one domain of the at least one biomarker forms an assay;
   wherein the presence of the at least one biomarker in the body fluid, whether analyzed in vivo or in vitro, indicates a vascular disease or disorder associated with aberrant ADAM30 expression or activity in the subject; and
   wherein formation of the assay determines when there is an increase in ADAM30 to administer a therapeutically effective amount of a therapeutic agent to treat the vascular disease or disorder.

2. The method of claim 1, wherein the biomarker has a genetic sequence of SEQ. ID. NO.: 1.

3. The method of claim 1, further comprising identifying Sturge-Weber syndrome via the presence of the at least one biomarker.

4. The method of claim 1, further comprising differentiating cancer cell subtypes via the presence of the at least one biomarker.

\* \* \* \* \*